United States Patent
Sydlik et al.

(10) Patent No.: US 11,292,760 B2
(45) Date of Patent: Apr. 5, 2022

(54) THERAPEUTIC ACRYLATES AS ENHANCED MEDICAL ADHESIVES

(71) Applicant: Carnegie Mellon University, Pittsburgh, PA (US)

(72) Inventors: Stefanie A. Sydlik, Pittsburgh, PA (US); Zoe Wright, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 16/332,511

(22) PCT Filed: Sep. 13, 2017

(86) PCT No.: PCT/US2017/051271
§ 371 (c)(1),
(2) Date: Mar. 12, 2019

(87) PCT Pub. No.: WO2018/052936
PCT Pub. Date: Mar. 22, 2018

(65) Prior Publication Data
US 2019/0262497 A1    Aug. 29, 2019

Related U.S. Application Data

(60) Provisional application No. 62/495,412, filed on Sep. 13, 2016.

(51) Int. Cl.
| | |
|---|---|
| *C07D 251/42* | (2006.01) |
| *C07D 251/48* | (2006.01) |
| *C07D 251/54* | (2006.01) |
| *C07C 65/10* | (2006.01) |
| *A61L 24/00* | (2006.01) |
| *A61K 47/54* | (2017.01) |
| *C07C 57/42* | (2006.01) |
| *C07C 327/34* | (2006.01) |
| *C07C 233/55* | (2006.01) |
| *C07D 251/18* | (2006.01) |
| *A61P 29/00* | (2006.01) |
| *C07C 323/59* | (2006.01) |
| *C07C 233/25* | (2006.01) |
| *C08F 222/32* | (2006.01) |

(52) U.S. Cl.
CPC ............. *C07C 65/10* (2013.01); *A61K 47/54* (2017.08); *A61L 24/0015* (2013.01); *A61P 29/00* (2018.01); *C07C 57/42* (2013.01); *C07C 233/25* (2013.01); *C07C 233/55* (2013.01); *C07C 323/59* (2013.01); *C07C 327/34* (2013.01); *C07D 251/18* (2013.01); *C08F 222/324* (2020.02); *A61L 2300/402* (2013.01); *A61L 2300/41* (2013.01); *A61L 2300/428* (2013.01); *A61L 2300/80* (2013.01)

(58) Field of Classification Search
CPC ... C07D 251/42; C07D 251/48; C07D 251/54

USPC .................. 544/194, 196, 204; 514/245, 241
See application file for complete search history.

(56) References Cited

U.S. PATENT DOCUMENTS

| | | | |
|---|---|---|---|
| 5,328,687 | A | 7/1994 | Leung et al. |
| 5,945,457 | A | 8/1999 | Plate et al. |
| 2005/0095529 | A1 | 5/2005 | Sugasaki et al. |
| 2011/0230561 | A1 | 9/2011 | Liu et al. |

FOREIGN PATENT DOCUMENTS

| | | | | |
|---|---|---|---|---|
| IL | 234250 | * | 8/2014 | ............... A61L 2/00 |
| WO | 9916475 | A2 | 4/1999 | |
| WO | WO-9919309 | A1 * | 4/1999 | ........... C07D 405/12 |

OTHER PUBLICATIONS

PubChem Database Compound, NSC372151, Available Date Mar. 26, 2005.*
Babazadeh; "Design, synthesis and in vitro evaluation of vinyl ether type polymeric prodrugs of ibuprofen, ketoprofen and naproxen", International Journal of Pharmaceutics, 2008, pp. 167-173, vol. 356.
Babazadeh, "Synthesis and in vitro evaluation of acrylate-based macromolecular prodrugs containing mesalazine for colon-specific drug delivery", Der Pharma Chemica, 2014, pp. 411-419, vol. 6:3.
Babazadeh et al., "Synthesis, Characterization, and In Vitro Evaluation of New Ibuprofen Polymeric Prodrugs Based on 2-Hydroxypropyl Methacrylate", Sci Pharm, 2013, pp. 281-296, vol. 81.
Basu et al., "PEG-Biscyanoacrylate Crosslinker for Octyl Cyanoacrylate Bioadhesive", Macromol. Rapid Commun, 2016, pp. 251-256, vol. 37.
Corry et al., "Assessment of acrylic bone cement as a local delivery vehicle for the application of non-steroidal anti-inflammatory drugs", Biomaterials, 1998, pp. 1295-1301, vol. 19.
Davaran et al., "Acrylic type polymers containing ibuprofen and indomethacin with difunctional spacer group: synthesis and hydrolysis", Journal of Controlled Release, 1997, pp. 41-49, vol. 47.
Davaran et al., "Synthesis and Characterization of Methacrylic Derivatives of 5-Amino Salicylic Acid with pH-Sensitive Swelling Properties", AAPS PharmSciTech, 2001, pp. 80-85, vol. 2:4.
Dholakiya et al., "Novel acrylic copolymers derived from Paracetamol: Determination of reactivity ratio, microbial screening and thermal properties", Der Chemica Sinica, 2011, pp. 112-128, vol. 2:6.
Licea-Claverie et al., "A facile synthesis route for carboxyaryl-methacrylates: a way to obtain aromatic polyelectrolytes", Designed Monomers and Polymers, 2003, pp. 67-80, vol. 6:1.
Magana et al., "Polymeric prodrug-functionalized polypropylene films for sustained release of salicylic acid", International Journal of Pharmaceutics, 2016, pp. 579-585, vol. 511.
Mizrahi et al., "Anhydride Prodrug of Ibuprofen and Acrylic Polymers", AAPS PharmSciTech, 2009, pp. 453-458, vol. 10:2.

(Continued)

*Primary Examiner* — Brenda L Coleman
(74) *Attorney, Agent, or Firm* — The Webb Law Firm

(57) ABSTRACT

Provided herein are therapeutic acrylate compounds useful as medical adhesives, comprising a therapeutic agent covalently linked to a methacrylate or cyanoacrylate moiety. Adhesive compositions and kits, such as liquid sutures and bone cement also are provided along with uses for the compositions.

13 Claims, 12 Drawing Sheets

Specification includes a Sequence Listing.

(56) References Cited

OTHER PUBLICATIONS

Shergold et al., "The uniaxial stress versus strain response of pig skin and silicone rubber at low and high strain rates", International Journal of Impact Engineering, 2006, pp. 1384-1402, vol. 32.

Wang et al., "Tailor-made gemcitabine prodrug nanoparticles from well-defined drug-polymer amphiphiles prepared by controlled living radical polymerization for cancer chemotherapy", Journal of Materials Chemistry B, 2014, pp. 1891-1901, vol. 2:13.

Wong et al., "A Novel Low-Molecular-Weight Compound Enhances Ectopic Bone Formation and Fracture Repair", J Bone Joint Surg Am., 2013, pp. 454-461, vol. 95.

Wright et al., "Therapeutic adhesives: covalently modified acrylates for enhanced, injury-specific wound healing", Front. Bioeng. Biotechnol. Conference Abstract, 10th World Biomaterials Congress, 2016, 2 pages.

Wright et al., "Covalently-controlled drug delivery via therapeutic methacrylic tissue adhesives", J. Mater. Chem. B., 2017, pp. 7743-7755, vol. 5:37.

Anastasiou et al., "Aminosalicylate-Based Biodegradable Polymers: Syntheses and in vitro Characterization of Poly(anhydride-ester)s and Poly(anhydride-amide)s", Journal of Polymer Science: Part A: Polymer Chemistry, 2003, pp. 3667-3679, vol. 41, No. 22.

Autian, "Structure-Toxicity Relationships of Acrylic Monomers", Environmental Health Perspectives, 1975, pp. 141-152, vol. 11.

Babazadeh, "Synthesis and study of controlled release of ibuprofen from the new acrylic type polymers", International Journal of Pharmaceutics, 2006, pp. 68-73, vol. 316.

Bakopoulou et al., "Molecular Toxicology of Substances Released from Resin-Based Dental Restorative Materials", International Journal of Molecular Sciences, 2009, pp. 3861-3899, vol. 10.

Cameron et al., "The degradation of cyanoacrylate tissue adhesive", Surgery, 1965, pp. 424-430, vol. 58.

Cameron et al., "Cyanoacrylate applications in the GI Tract", Gastrointestinal Endoscopy, 2013, pp. 846-857, vol. 77, No. 6.

Cervantez-Uc et al., "Comparative study on the properties of acrylic bone cements prepared with either aliphatic or aromatic functionalized methacrylates", Biomaterials, 2005, pp. 4063-4072, vol. 26.

Chikakane et al., "Measurement of Skin pH and its Significance in Cutaneous Diseases", Clinics in Dermatology, 1995, pp. 299-306, vol. 13.

Coulthard et al., "Tissue adhesives for closure of surgical incisions", Cochrane Database of Systematic Reviews, 2010, 3 pages.

Dean, "Comparing NSAIDS", PubMed Clinical Q&A, 2011, 3 pages.

Duarte et al., "Surgical Adhesives: Systematic review of the main types and development forecast", Progress in Polymer Science, 2012, pp. 1031-1050, vol. 37.

Dumville et al., "Tissue adhesives for closure of surgical incisions (Review)", The Cochrane Library, 2014, Issue 11.

Erdmann et al., "Synthesis and degradation characteristics of salicylic acid-derived poly(anhydride-esters)", Biomaterials, 2000, pp. 1941-1946, vol. 21.

Feretis et al., "Endoscopic Homeostasis of Esophageal and Gastric Variceal Bleeding with Histoacryl", Endoscopy, 1990, pp. 282-284, vol. 22.

Ferracane et al., "Elution of leachable components from composites", Journal of Oral Rehabilitation, 1994, pp. 441-452, vol. 21.

Fujii et al., "Sulfone-Containing Methacrylate Homopolymers: Wetting and Thermal Properties", Langmuir, 2016, pp. 765-771, vol. 32.

Gallardo et al., "Synthesis and characterization of a new poly(methacrylamide) bearing side groups of biomedical interest", Polymer, 1993 , pp. 394-400, vol. 34, No. 2.

Gallardo et al., "NSAIDS bound to methacrylic carriers: microstructural characterization and in vitro release analysis", Journal of Controlled Release, 2001, pp. 127-140, vol. 71.

Göpferich, "Mechanisms of polymer degradation and erosion", Biomaterials, 1996, pp. 103-114, vol. 17, No. 2.

Göpferich et al., "Polyanhydride degradation and erosion". Advanced Drug Delivery Reviews, 2002, pp. 911-931, vol. 54, No. 7.

Gosavi et al., "Local and Systemic Effects of Unpolymerised Monomers", Dental Research Journal, 2010, pp. 82-87, vol. 7, No. 2.

Green, "Understanding NSAIDS: From Aspirin to COX-2", Clinical Cornerstone: Sports Medicine, 2001, pp. 50-59, vol. 3, No. 5.

Greim et al., "Assessment of structurally related chemicals: toxicity and ecotoxicity of acrylic acid and acrylic acid alkyl esters (acrylates), methacrylic acid and methacrylic acid alkyl esters (methacrylates)", Chemosphere, 1995,pp. 2637-2659, vol. 31, No. 2.

Grimaldi et al., "Octyl-2-cyanoacrylate Adhesive for Skin Closure: Eight Years Experience", In Vivo, 2015, pp. 145-148, vol. 29.

Han et al., "Synthesis and degradation behavior of poly(ethyl cyanoacrylate)", Polymer Degradation and Stability, 2008, pp. 1243-1251, vol. 93.

Islas-Blancas et al., "Characterization of bone cements prepared with functionalized methacrylates and hydroxyapatite", Journal of Biomaterials Science, Polymer Edition, 2001, pp. 893-910, vol. 12, No. 8.

Jarosz et al., "Oxidative Stress and Mitochondrial Activation as the Main Mechanisms Underlying Graphene Toxicity against Human Cancer Cells", Oxidative Medicine and Cellular Longevity, 2016, 14 pages, vol. 2016, Article ID No. 5851035.

Kato et al., "A synthetic compound that potentiates bone morphogenetic protein-2-induced transdifferentiation of myoblasts into the osteoblastic phenotype", Molecular and Cellular Biochemistry, 2011, pp. 97-106, vol. 349, Nos. 1-2.

Krifka et al. "A review of adaptive mechanisms in cell responses towards oxidative stress caused by dental resin monomers", Biomaterials, 2013, pp. 4555-4563, vol. 34.

Lambers et al., "Natural skin surface pH is on average below 5, which is beneficial for its resident flora", International Journal of Cosmetic Science, 2006, pp. 359-370, vol. 28.

Langer et al., "Tissue Engineering", Science, New Series, 1993, pp. 920-926, vol. 260, No. 5110.

Lewis, "Properties of Acrylic Bone Cement: State of the Art Review", Journal of Biomedical Materials Research, 1997, pp. 155-182, vol. 38, No. 2.

Linden, Jr. et al., "Performance of Modified Cyanoacrylate Composition as Tissue Adhesives for Soft and Hard Tissues", Journal of Biomedical Materials Research, 1997, pp. 348-355, vol. 38, No. 4.

Martin et al., "Endoscopic control of massive upper gastrointestinal bleeding with a tissue adhesive (MBR 4197)", Gastrointestinal Endoscopy, 1977, pp. 74-76, vol. 24, No. 2.

Mizrahi et al., "Anhydride Prodrug of Ibuprofen and Acrylic Polymers", AAPS PharmSciTech, 2009, pp. 453-458, vol. 10, No. 2.

Rawicz, "Acute postoperative pain in children", Anaesthesiology Intensive Therapy, 2015, pp. 263-265, vol. 47, No. 3.

Reynolds et al., "Non-Steroidal Anti-Inflammatory Drug (NSAID)—Derived Poly(anhydride-esters) in Bone and Periodontal Regeneration", Current Drug Delivery, 2007, pp. 233-239, vol. 4, No. 3.

Robinson et al., "Mechanical properties of poly(methyl methacrylate) bone cements", Journal of Biomedical Materials Research, 1981, pp. 203-208, vol. 15.

Sabino et al., "Physicochemical, Mechanical, and Biological Properties of Bone Cements Prepared with Functionalized Methacrylates", Journal of Biomaterials Applications, 2004, pp. 147-161, vol. 19.

Santerre et al., "Relation of dental composite formulations to their degradation and the release of hydrolyzed polymeric-resin-derived products", Critical Reviews in Oral Biology and Medicine, 2001, pp. 136-151, vol. 12, No. 2.

Schmeltzer et al., "Synthesis and Cytotoxicity of Salicylate-Based Poly(anhydride esters)", Biomacromolecules, 2005, pp. 359-367, vol. 6, No. 1.

Shinzato et al., "PMMA-based bioactive cement: Effect of glass bead filler content and histological change with time", Journal of Biomedical Materials Research, 2002, pp. 225-232, vol. 59, No. 2.

Toriumi et al., "Histotoxicity of Cyanoacrylate Tissue Adhesives: A Comparative Study", Archives of Otolaryngology—Head and Neck Surgery, 1990, pp. 546-550, vol. 116, No. 5.

Ueno et al. "N-acetyl cysteine protects osteoblastic function from oxidative stress", Journal of Biomedical Materials Research Part A, 2011, pp. 523-531, vol. 99A.

(56) References Cited

OTHER PUBLICATIONS

Uhrich et al., "Polymeric Systems for Controlled Drug Release", Chemical Reviews, 1999, pp. 3181-3198, vol. 99, No. 11.

Vazquez et al., "Reactivity of a polymerizable amine activator in the free radical copolymerization with methyl methacrylate and surface properties of copolymers", Polymer, 1997, pp. 4365-4372, vol. 38, No. 17.

Wu et al., Advanced Bioactive Inorganic Materials for Bone Regeneration and Drug Delivery, 2012, 119 pages, CRC Press, Boca Raton, US.

Yang et al., "Fatigue of the bone/cement interface and loosening of total joint replacements", International Journal of Fatigue, 2010, pp. 1639-1649, vol. 32.

Whitaker-Brothers et al., "Investigation into the erosion mechanism of salicylate-based poly(anhydride-esters)", Journal of Biomedical Materials Research Part A, 2006, pp. 470-479, vol. 76A, No. 3.

"Summary of Safety and Effectiveness Data: DERMABOND (a formulation of 2-octyl cyanoacrylate)", Food and Drug Administration, Aug. 26, 1998.

"Summary of Safety and Effectiveness Data: Histoacryl and Histoacryl Blue", Food and Drug Administration, Feb. 16, 2007, 12 pages.

\* cited by examiner

THERAPEUTIC ACRYLATES AS ENHANCED MEDICAL ADHESIVES

CROSS REFERENCE TO RELATED APPLICATIONS

This application is the United States national phase of International Application No. PCT/US2017/051271 filed Sep. 13, 2017, and claims the benefit of U.S. Provisional Patent Application No. 62/495,412 filed Sep. 13, 2016, each of which is incorporated herein by reference in its entirety.

The Sequence Listing associated with this application is filed in electronic format via EFS-Web and is hereby incorporated by reference into the specification in its entirety. The name of the text file containing the Sequence Listing is 1901296_ST25.txt. The size of the text file is 2,420 bytes, and the text file was created on Mar. 12, 2019.

Provided herein are therapeutic acrylates useful as medical adhesives, and uses therefor.

Medical adhesives are an exciting emerging technology for wound closure and medical device fixation. Acrylate-based adhesives have applications as bone and dental cements (methacrylate, MA), as well as liquid sutures for soft tissues (cyanoacrylate, CA). Acrylate adhesives offer advantages over traditional fixation methods (e.g. sutures and staples), including immediate and secure attachment, non-traumatic wound closure, and elimination of fixture removal. These materials cure quickly and accurately, and in many situations provide superior cosmetic results.

Because of their convenience and effectiveness, significant interest has been generated recently in expanding the application of acrylate adhesives to more facets of wound care. MA bone cements have been mixed with bioactive additives in an attempt to achieve enhanced, guided bone healing. So called "instant-cure" CAs are candidates for non-invasively sealing incisions from laparoscopic surgeries and rapidly providing hemostasis in emergency situations involving internal hemorrhaging. Additionally, CA adhesives are estimated to be capable of completely replacing sutures in about one third of all injuries requiring cutaneous wound closure.

Unfortunately, barriers exist to realizing the full potential of acrylate adhesives in many wound care applications. Brittleness and mismatch between mechanical properties of the adhesive and the tissue substrate can lead to failure at the adhesive-tissue junction: a common failure mode for both CA skin adhesives and MA cements. For example, fear of wound dehiscence from brittle adhesives is the major reason surgeons opt for sutures rather than CA adhesives. Further, current acrylate monomers exhibit significant cytotoxicity, caused by the reactivity of the monomer with tissue before the adhesive resin is fully cured, the exothermicity of polymerization during curing, and the release of toxic degradation products after curing. In terms of adhesive lifetime in vivo, both CAs and MAs suffer from a lack of control over degradation rate. CAs are unstable to moisture and release bursts of toxic formaldehyde as they degrade. MAs may release toxic species such as bis-phenol A through hydrolysis of their side groups, but because the polymer main chain remains uncleaved, MAs are otherwise bioinert and block the cell adhesion and ingrowth that stabilize adhered implants in the long run. Overall, current adhesives lack a straightforward venue through which adhesive mechanical properties, monomer toxicity, and adhesive degradation in vivo can be tuned.

Current products have tried to address patient discomfort and cytotoxicity of acrylate adhesives in two main ways. One strategy involves coupling pain relievers and other therapeutics with existing wound closure strategies. Sutures that elute therapeutics are currently available and offer promise for smoother and less painful healing. Similar approaches have been applied to allow delivery of therapeutics from bone cement. However, these technologies rely on physical processing to encapsulate the therapeutic moieties and therefore do not offer good control over release kinetics. Further, since the monomer structure remains unchanged, toxicity remains an issue with current acrylate materials.

The second strategy used by current products to address the cytotoxicity of acrylate adhesives involves manipulating the chemical structure of the monomer. Commercial medical adhesive products utilize monomers with large side groups such as alkyl chains, ethylene glycol oligomers, urethanes, and phenolic derivatives to help moderate monomer diffusion and reactivity. However, because the majority of substituents in these acrylates are tethered via hydrolytically unstable ester linkages, even cured resins can leech undesirable and potentially toxic degradation products. Substituted CAs also remain susceptible to the degradation pathways that produce formaldehyde. These modified, bulky monomers represent improvement over earlier generations of acrylate adhesives, but do not overcome the barriers that prevent acrylates from reaching their full potential as medical tools.

SUMMARY

To improve upon existing technology, provided herein are compositions and methods that directly couple therapeutic agents to acrylate monomers using chemical bonds that can be predictably cleaved under physiological conditions for controlled release. In aspects, by chemically linking therapeutics to acrylate monomers, monomer toxicity is reduced, patient discomfort is decreased, and release of therapeutics over time is predictable and tunable. Using a variety of chemical bonds, different controlled release profiles and/or permanent covalent attachment can be accessed. This technology enhances medical adhesives by simultaneously improving monomer biocompatibility and adding therapeutic value.

The compositions and methods described herein can be used to adapt medical adhesives directly to a wide variety of uses. Tethering therapeutics via an anhydride bond, which degrades quickly in aqueous environments, can provide a burst release useful to mitigate pain during wound closure. Amide bonds, by contrast, are stable to hydrolysis and can be used to tether signaling moieties directly at the site of injury—useful for directed healing at tissue-implant interfaces. Ester bonds have intermediate stability in water, and will therefore release therapeutics slowly and for more extended periods of time. Release of therapeutics can be further tailored simply by mixing a combination of these monomer types in particular proportions to create a composite material suited to a specific injury. Further, in aspects, a class of acrylate monomers is provided that can seamlessly integrate into commercial adhesives to further enable variety and ease of use. These materials offer promise of a convenient method of closure or fixation that will result in faster, directed healing and less pain.

In one aspect an acrylate compound is provided comprising one or more acrylate moieties covalently linked to a therapeutic agent moiety by an anhydride bond, a thioester bond, an ester bond, or an amide bond, for example and without limitation having the structure:

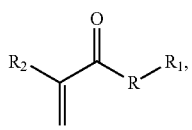

where R is an anhydride bond, a thioester bond, an ester bond, or an amide bond, $R_1$ is a therapeutic agent moiety, and $R_2$ is a cyano or methyl group, or a polymer thereof, wherein when R is ester and $R_2$ is methyl, $R_1$ is not a salicylic acid moiety. In one aspect, a composition is provided, comprising the compound or a polymer including a residue of the compound. In another aspect, an adhesive composition is provided. The adhesive composition comprises a therapeutic acrylate monomer having the structure

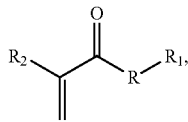

where R is an anhydride bond, a thioester bond, an ester bond, or an amide bond, $R_1$ is a therapeutic agent moiety, and $R_2$ is a cyano or methyl group; and a solvent for the acrylate monomer. The adhesive composition optionally comprises a second cyanoacrylate or methacrylate adhesive monomer that is optionally a second therapeutic acrylate monomer.

In a further aspect, a bone cement kit is provided. The kit comprises a first vessel containing an acrylate polymer powder, and a second vessel comprising a liquid acrylate adhesive, wherein either the acrylate polymer powder comprises a residue of a therapeutic acrylate monomer, or the liquid acrylate adhesive comprises a therapeutic acrylate monomer, and wherein the therapeutic acrylate monomer has the structure

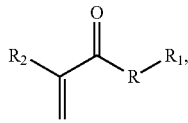

where R is an anhydride bond, a thioester bond, an ester bond, or an amide bond, $R_1$ is a therapeutic agent moiety, and $R_2$ is a cyano or methyl group.

According to yet another aspect of, a method of treating a patient is provided, comprising joining tissue in the patient with an acrylic adhesive comprising an acrylate compound comprising one or more acrylate moieties covalently linked to a therapeutic agent moiety by an anhydride bond, a thioester bond, an ester bond, or an amide bond, for example and without limitation having the structure:

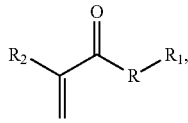

where R is an anhydride bond, a thioester bond, an ester bond, or an amide bond, $R_1$ is a therapeutic agent moiety, and $R_2$ is a cyano or methyl group, or a polymer thereof. In one aspect, a composition is provided, comprising the compound or a polymer including a residue of the compound.

Overall, the TMA materials resulted in similar if not significantly higher cytocompatibility compared to Vetbond™ (+) BPO, DMPT.

Figure 6:
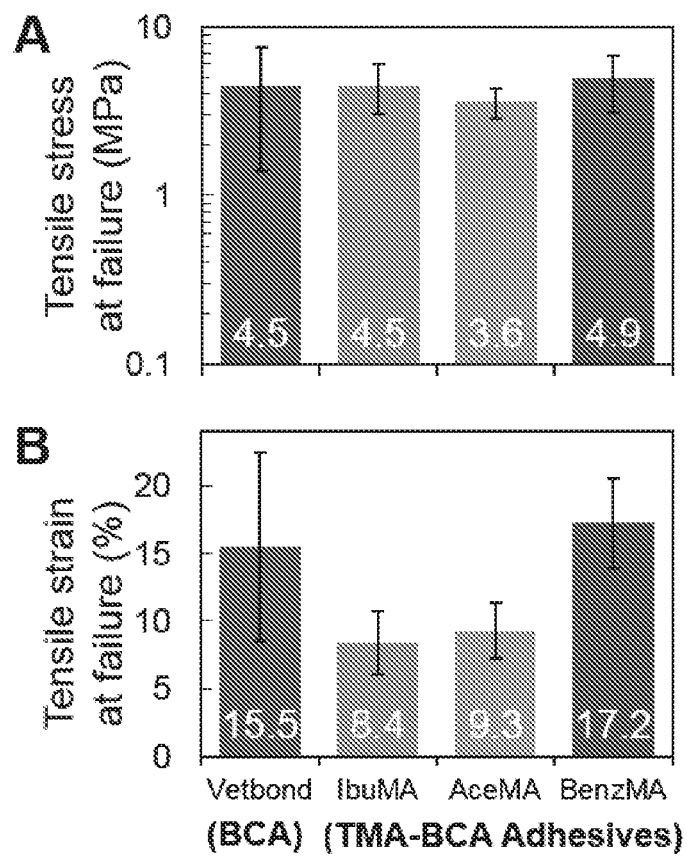

FIG. 6. TMA-BCA adhesives evaluated in tension via a wound closure model using porcine skin, in accordance with ASTM F2458-05(2015). A) Tensile stress was calculated by dividing axial force (N) at failure by the product of incision width and adhesive layer thickness ($m^2$). B) Strain percent was calculated by dividing sample length between the instrument grips (mm) by displacement (mm) at adhesive failure.

Figure 7:
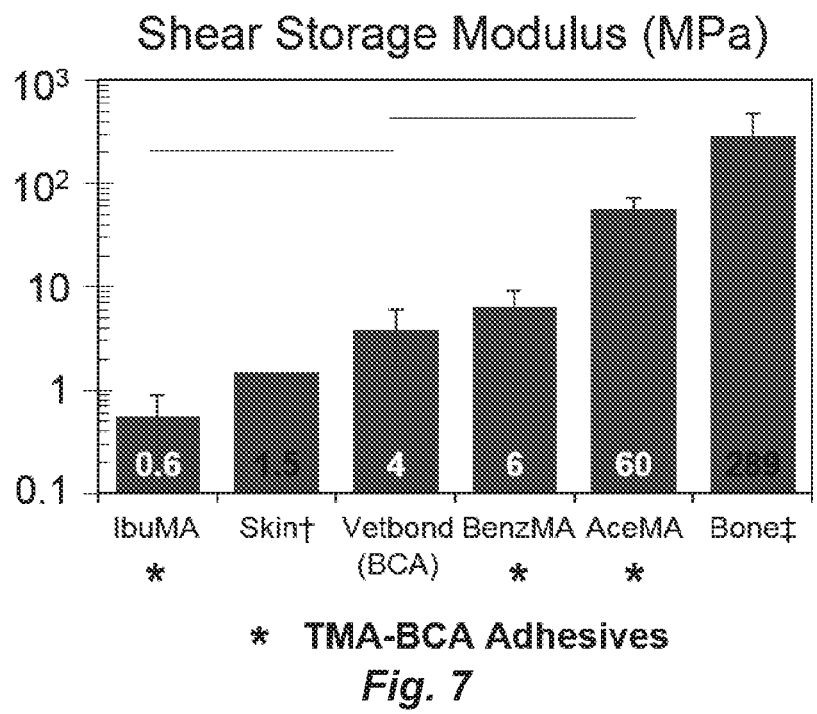

FIG. 7. Shear storage moduli for TMA-BCA adhesives, determined at 1 Hz and 1% strain, which are presented as an indication of the stiffness of the adhesives. Adhesives were cured directly between 8 mm disposable aluminum plates at 37° C. Lines denote statistically significant differences compared to Vetbond™ (BCA). †As quantified by O. A. Shergold, et al., The uniaxial stress versus strain response of pig skin and silicone rubber at low and high strain rates, Int J. Impact Eng., 2006, 32, 1384-140. ‡As quantified by Gamier et al. (K. B. Gamier, et al., Med. Eng. Phys., 1999, 21, 641-649).

Figure 8:
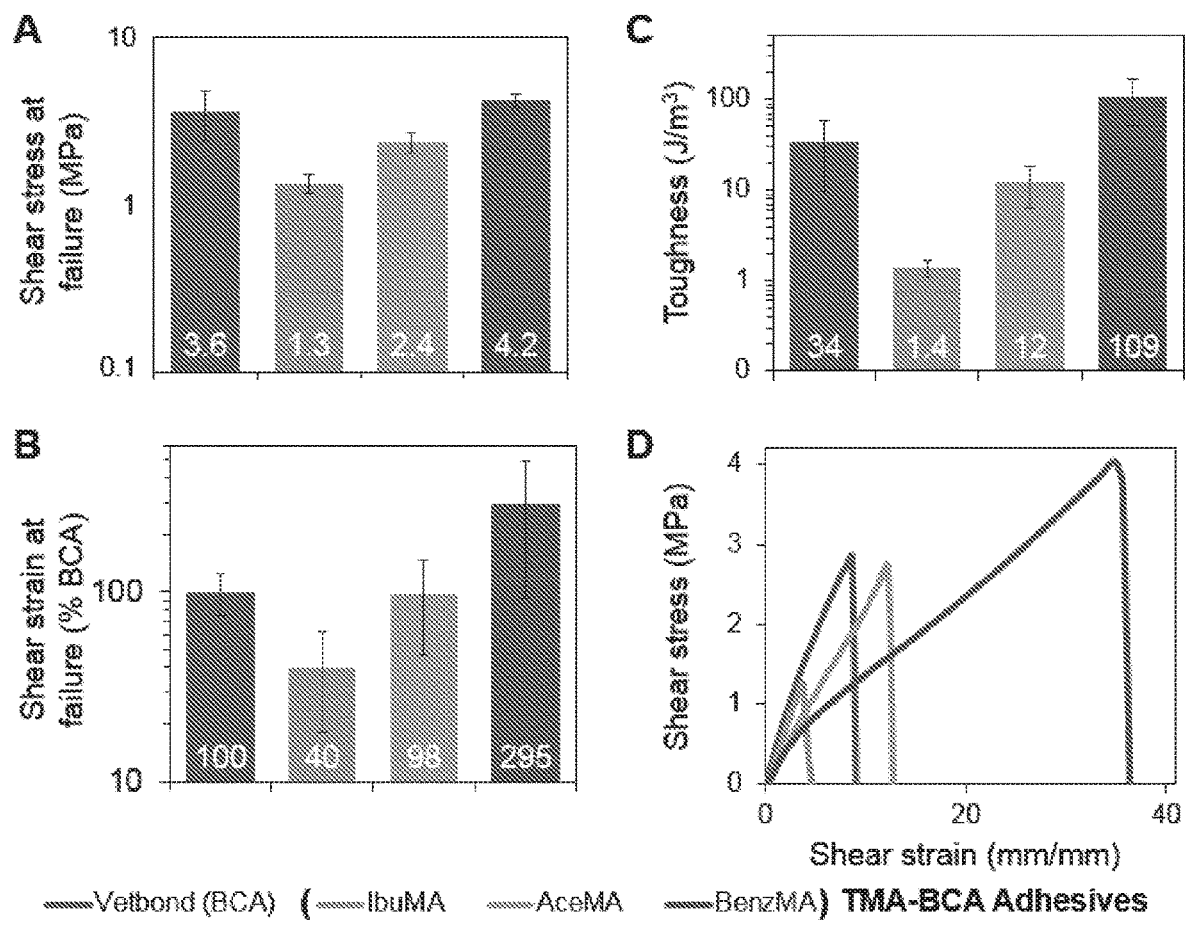

FIG. 8. Lap shear data, collected in accordance with ASTM D1002-10, for TMA-BCA adhesives, including: A) shear stress at failure, calculated as the peak load (N) divided by adhesive area ($m^2$), B) shear strain at failure, calculated as adhesive thickness (mm) divided by displacement (mm) and normalized to the Vetbond™ control, C) toughness, calculated from the area under the stress-strain curves for each adhesive, and normalized to Vetbond™, and D) representative stress-strain curves for each adhesive.

Figure 9A:
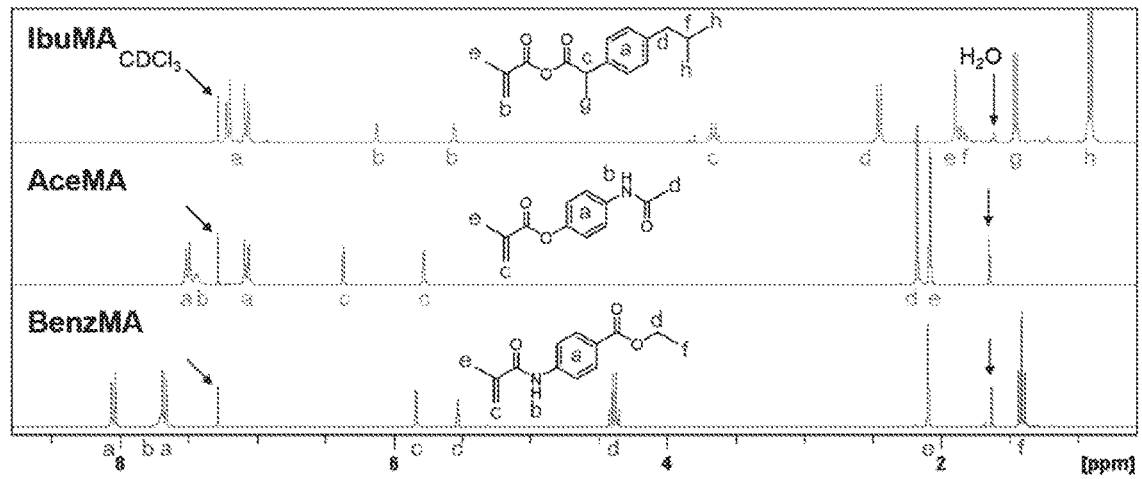
Figure 9B:
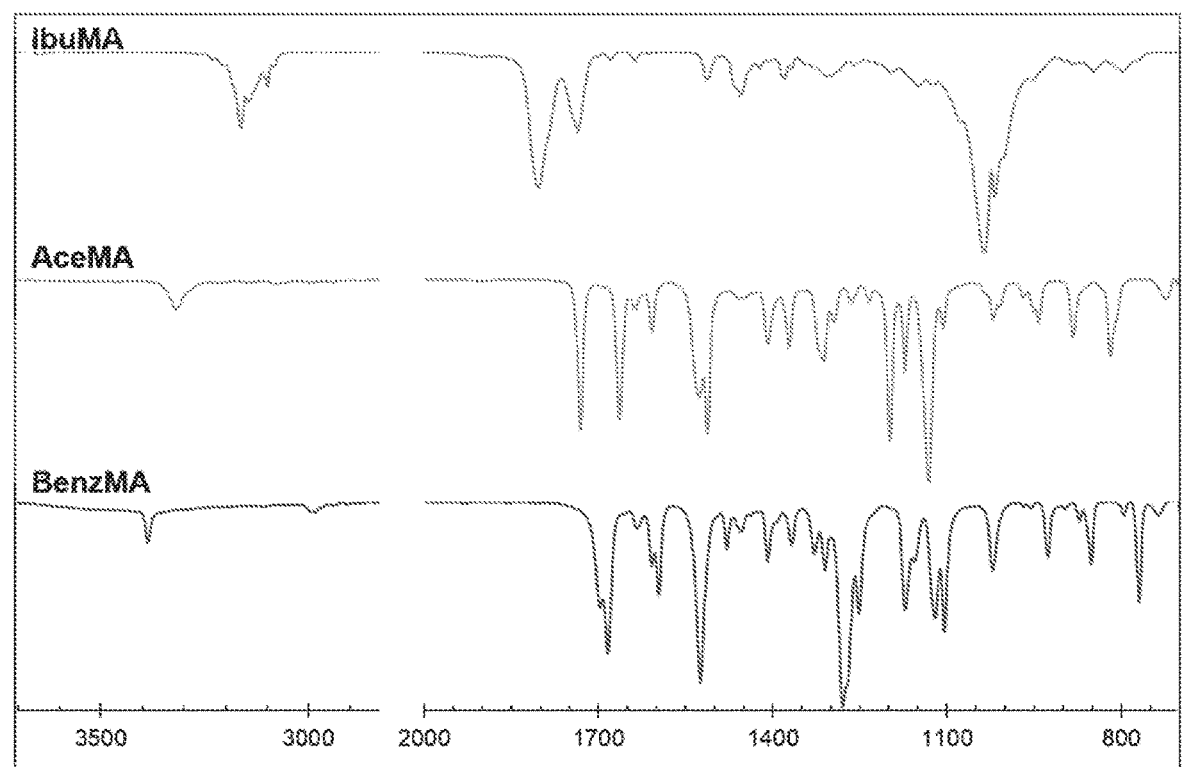

FIGS. 9A and 9B. FIG. 9A) $^1$H NMR (300 MHz) of TMA monomers in $CDCl_3$. Arrows indicate solvent peaks. FIG. 9B) FT-IR spectra of TMA monomers acquired neat using a Germanium ATR crystal.

Figure 10:
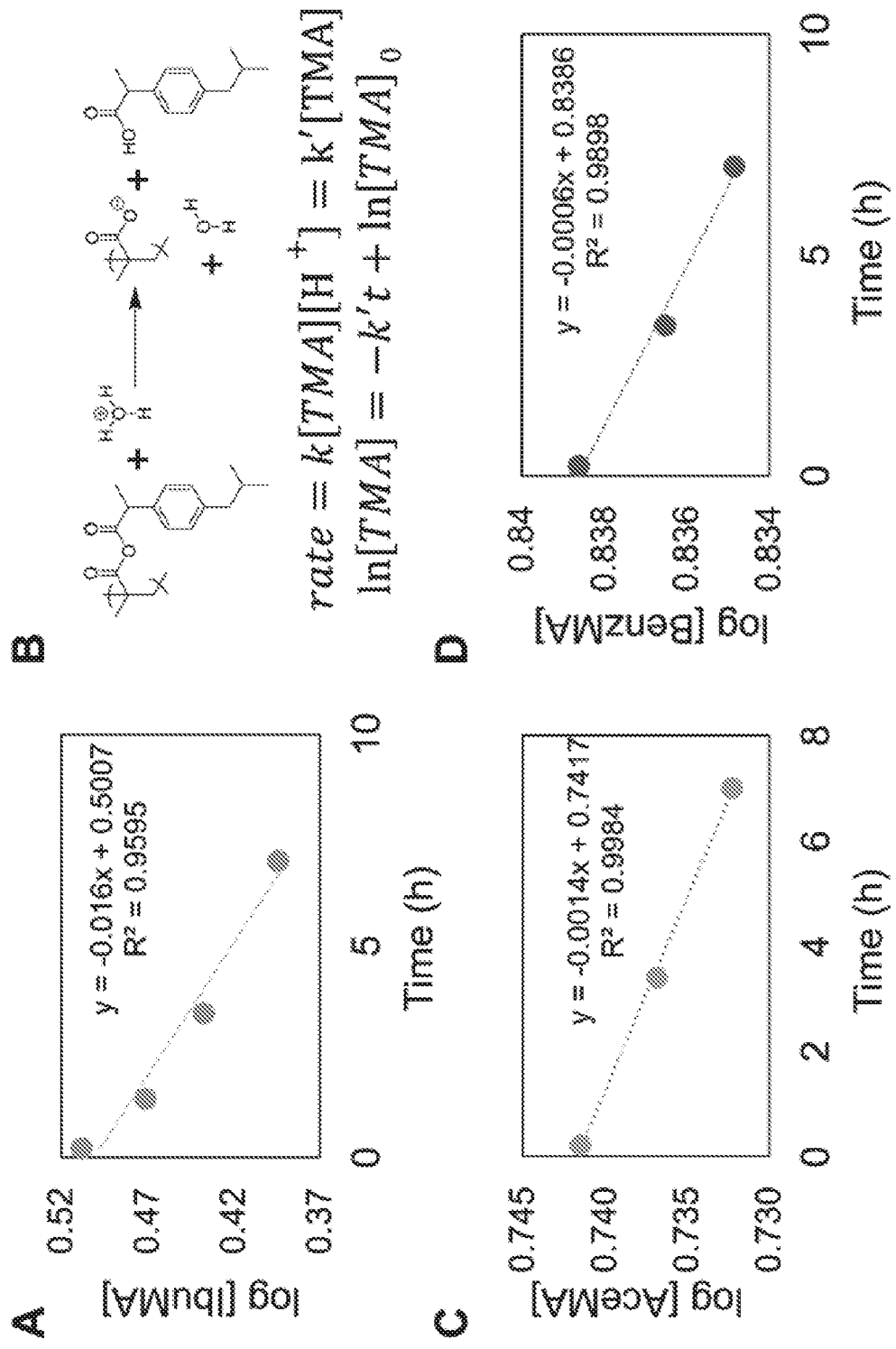

FIG. 10. Plots of log [TMA] versus time for A) IbuMA, C) AceMA, and D) BenzMA used to determine the rate constants of hydrolysis/therapeutic release from TMA-BCA adhesives in sodium acetate buffer (pH 4.9). Unhydrolyzed TMA ([TMA]) was calculated from the concentration of free drug and the mass of TMA monomer applied in the adhesive. A pseudo-first order reaction rate was assumed in all cases because the acidic buffer provides a constant excess of protons. B) A representative hydrolysis reaction scheme and the corresponding pseudo-first order rate equation (above) and integrated rate law (below) is shown for IbuMA-BCA.

Figure 11:
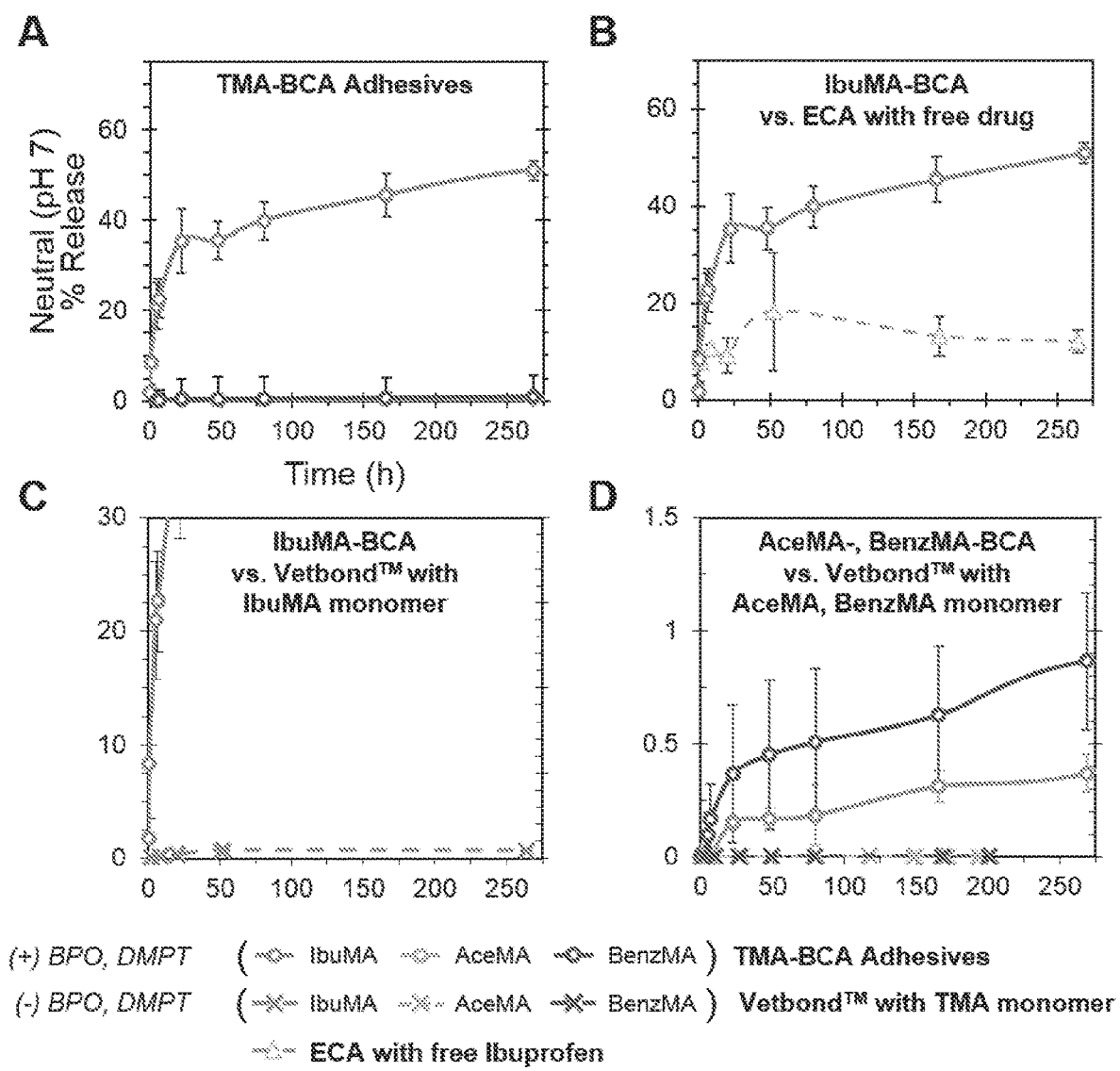

FIG. 11. Comparison of therapeutic release from TMA-BCA adhesives cured using the BPO-DMPT radical initiator-accelerator system with B) release of free ibuprofen from an ethyl cyanoacrylate (ECA) matrix (− BPO, DMPT), and C, D) release of therapeutics and/or TMA monomer (which are not directly distinguishable by ultraviolet-visible light absorption) from a Vetbond™ (BCA) matrix (− BPO, DMPT). A) shows therapeutic release from TMA-BCA adhesives (+ BPO, DMPT) as presented in FIG. 2, rescaled for ease of comparison with B-D. All experiments were performed in pH 7 deionized water.

Figure 12:
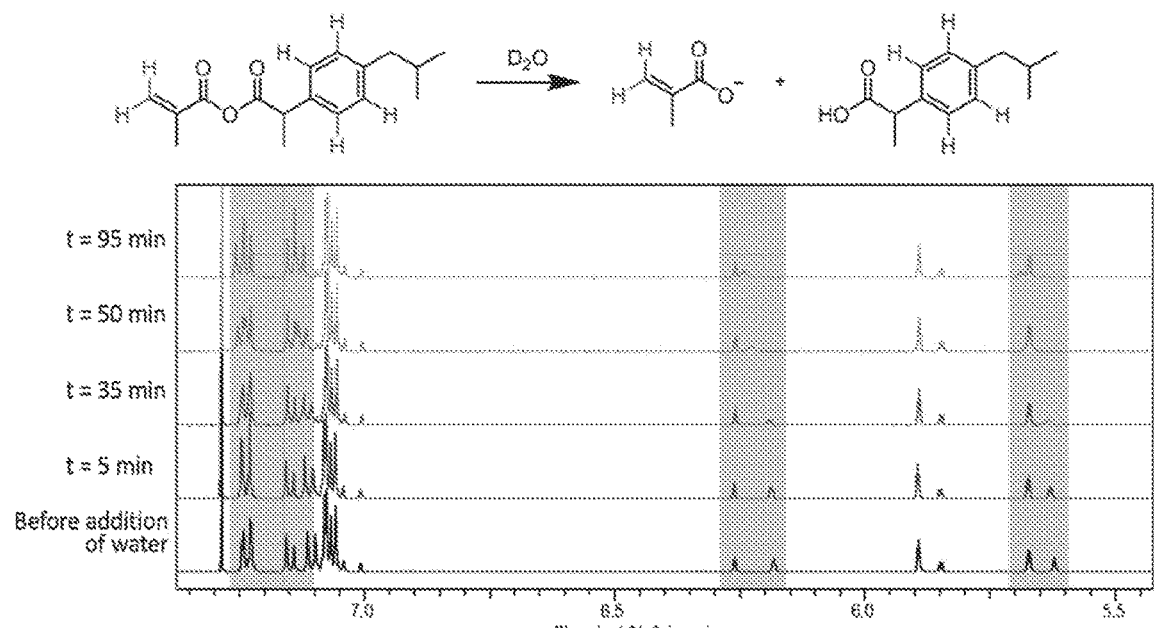

FIG. 12. $^1$H NMR (500 MHz) observation of reaction of oligo-IbuMA (dissolved in 90 μL $CDCl_3$) with $D_2O$ (10 μL). "Oligo-IbuMA" represents the mixture of IbuMA monomer, short-chained IbuMA oligomers containing a variety of end groups, and partially hydrolyzed IbuMA that is obtained upon exposure of IbuMA monomer to moist/ambient air. Over time following exposure to $D_2O$, the multiplets describing the mixture of IbuMA derivatives at t=0 are seen to converge, especially in the aromatic and vinylic regions, suggesting a homogenization of the IbuMA mixture through hydrolysis of the ibuprofen side group.

Figure 13:
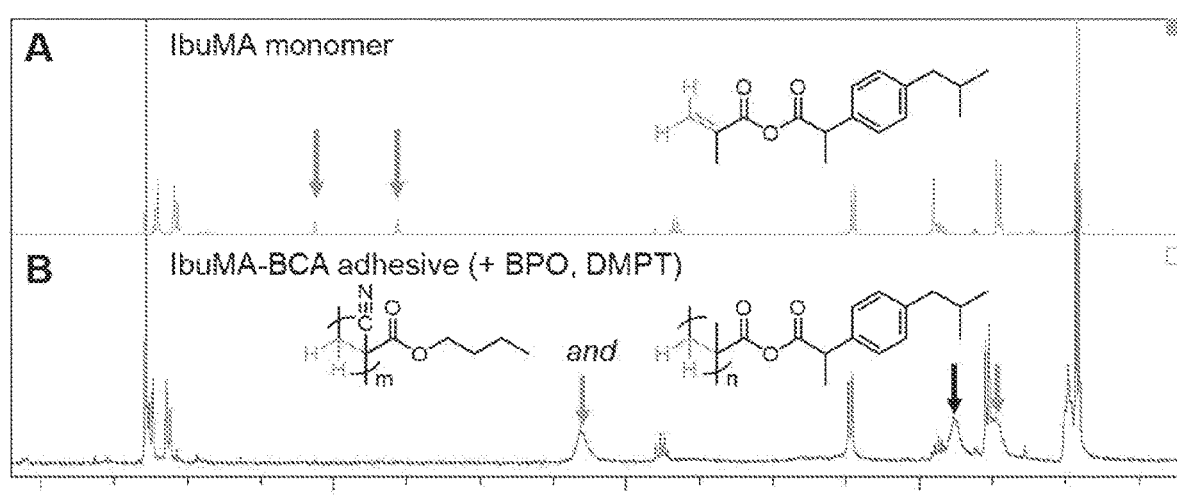

FIG. 13. Comparison of $^1$H NMR spectra (300 MHz, $CDCl_3$) of A) IbuMA monomer and B) cured IbuMA-BCA adhesive. (A) displays two signals (arrows at 5.57 and 6.14 ppm) that correspond to the vinyl protons of the IbuMA monomer, which is typical of acrylic-type monomers including cyanoacrylates and methacrylates. Vinyl peaks are not present in (B), indicating polymerization has occurred to completion. Instead, several broad peaks are visible, which are attributed to the same two protons when present in repeat units of polymers as opposed to vinyl-containing monomers. Signals labelled with blue, black, and orange arrows are attributed to protons neighbored only by cyanoacrylate repeat units, a mixture of cyanoacrylate and IbuMA units, and only IbuMA units, respectively. These signals suggest that copolymerization of BCA and IbuMA does occur during curing of the IbuMA-BCA adhesive.

Figure 14:
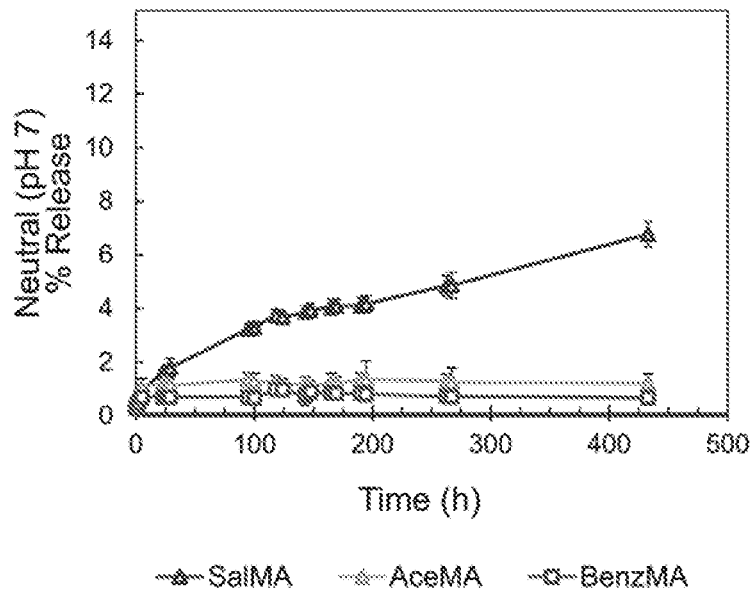

FIG. 14 is a graph showing controlled release of therapeutic agents as described in Example 6.

Figure 15:
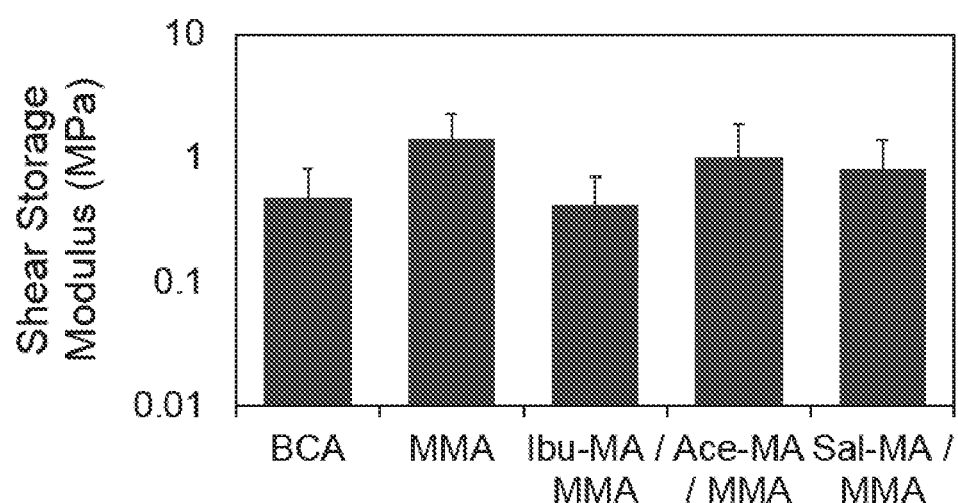

FIG. 15 is a graph depicting shear storage moduli of TMA-MMA adhesives, determined by rheometry, compared to BCA (Vetbond™) and MMA.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

As used herein, the term "polymer composition" is a composition comprising one or more polymers. As a class, "polymers" includes homopolymers, heteropolymers, co-polymers, block polymers, block co-polymers and can be both natural and synthetic.

Homopolymers contain one type of building block, or monomer, whereas co-polymers contain more than one type of monomer.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage, such as an ester, or amide linkage, if that linkage is present in the polymer.

A "moiety" is a part of a chemical compound, and includes groups, such as functional groups. As such, as therapeutic agent moiety is a therapeutic agent or compound that is modified by attachment to another compound moiety, such as a polymer monomer, e.g. the acrylate monomers described herein, or a polymer, such as an acrylic polymer as described herein.

"Therapeutic" refers to the ability of a compound or composition to elicit a beneficial or desirable effect in a patient, such as for treatment of a disease, wound, or condition, or for generating a desirable or beneficial effect such as, without limitation: anesthetic, analgesic, anti-inflammatory, cell homing, cell differentiation, cell growth stimulation, or anti-fibrotic effects.

As used herein, a "prodrug" is a compound or composition that is inactive, but is chemically modified in vivo to yield an active chemical entity.

A "functional group" or a "reactive group" is a reactive chemical moiety that can be used to covalently link a chemical compound to another chemical compound, such as include, for example and without limitation: hydroxyl, carbonyl, carboxyl, methoxycarbonyl, sulfonyl, thiol, amine, or sulfonamide.

The term "alkyl" refers to both branched and straight-chain saturated aliphatic hydrocarbon groups. These groups can have a stated number of carbon atoms, expressed as $C_{x-y}$, where x and y typically are integers. For example, $C_{5-12}$, includes $C_5$, $C_6$, $C_7$, $C_8$, $C_9$, $C_{10}$, $C_{11}$, or $C_{12}$. Alkyl groups include, without limitation: methyl, ethyl, propyl, isopropyl, n-, s- and t-butyl, n- and s-pentyl, hexyl, heptyl, octyl, etc. Alkyl groups include groups that have two or more points of attachment (e.g., alkylene), and cycloalkyl groups, which are saturated ring groups, such as cyclopropyl, cyclobutyl, or cyclopentyl.

An "acrylate" is a compound having the structure:

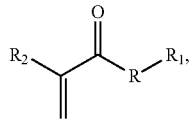

where R is any bond, but in the context of the monomers or compositions described herein, may be an anhydride bond, a thioester bond, an ester bond, or an amide bond. In aspects, relating to the monomers or compositions described herein, $R_1$ is a therapeutic agent moiety. For adhesives, $R_1$ may be a $C_1$-$C_{12}$ alkyl group. In aspects, $R_2$ is a cyano (—CN) or methyl (—CH$_3$) group, which are the most common groups used in acrylate adhesives, though $R_2$ may be, for example and without limitation, $C_{1-4}$ alkyl, NO$_2$, halo, or sulfone. Generally, useful commercial adhesives are methacrylates ($R_2$=methyl) and cyanoacrylates ($R_2$=cyano).

Acrylates are an important class of medical adhesives, with applications as bone and dental cements (methyl acrylate, MA) as well as liquid sutures (cyanoacrylate, CA). Using chemical bonds that can be predictably cleaved in physiological conditions, described herein are a family of modified acrylate monomers with reduced toxicity that incorporate covalently bonded therapeutic agent moieties. According to the type of chemical bond used to anchor the therapeutic agent moiety to the acrylate monomer, the adhesives will either elute therapeutics according to specific controlled release profiles, or anchor the therapeutics at the site of injury to signal for enhanced wound healing. These materials offer promise of a convenient method of closure or fixation that will result in faster, directed healing and less pain. Also provided are polymers, such as (poly)acrylate homopolymers or copolymers comprising (e.g. incorporating) any monomer as described herein.

In aspects, the compounds are substituted MA and CA monomers, with active substituents, e.g., therapeutic agents, covalently bonded at the carboxylic acid, and polymers comprising those substituted MA or CA monomers. In aspects, the therapeutic agent is a small-molecule therapeutic agent moiety, which is covalently bonded to either MA or CA. According to the chemistry of the covalent bond, the therapeutic agent moiety may either be anchored at the site of adhesive application (to serve as a signal to promote wound healing), or undergo controlled release in either a burst-release or a sustained-release profile. Due to the positioning of this side group, the mechanism of polymerization of these modified acrylate monomers will not be affected by the presence of the therapeutics.

In aspects, the modified acrylate monomers comprise three major components:
1. An acrylate backbone moiety of either a MA or CA;
2. A therapeutic agent moiety that serves as a side group on the acrylate monomer. Therapeutic moieties include but are not limited to compounds like non-steroidal anti-inflammatory drugs such as ibuprofen or acetaminophen, anesthetic drugs such as procaine or benzocaine, biologically active small-molecule signaling moieties such as SVAK-12, amino acids and modified amino acids such as N-acetyl cysteine, cytokines and chemokines, stem cell differentiation compounds, and other peptides such as RGD or DGEA; and
3. A covalent linkage between the backbone and the therapeutic moiety. In aspects, this linkage comprises, without limitation, one anhydride, ester, thioester, or amide bond.
4. In certain instances, e.g., to further modify a release profile, and where a therapeutic agent has multiple active groups through which an acrylate moiety can be linked, it might be desirable to link two or more acrylate moieties to a single therapeutic agent moiety. For example SVAK-12 has two amine groups that can be used independently to form one or two amide groups with acrylate moieties to produce mono- or di-acrylate-substituted SVAK-12.
5. Polymers of the modified acrylate monomers may be provided, that include homopolymers of the modified acrylate monomers and copolymers with a second acrylate monomer, such as a medically-acceptable methacrylate or cyanoacrylate adhesive, as are broadly-known and are commercially available.

Figure 1:
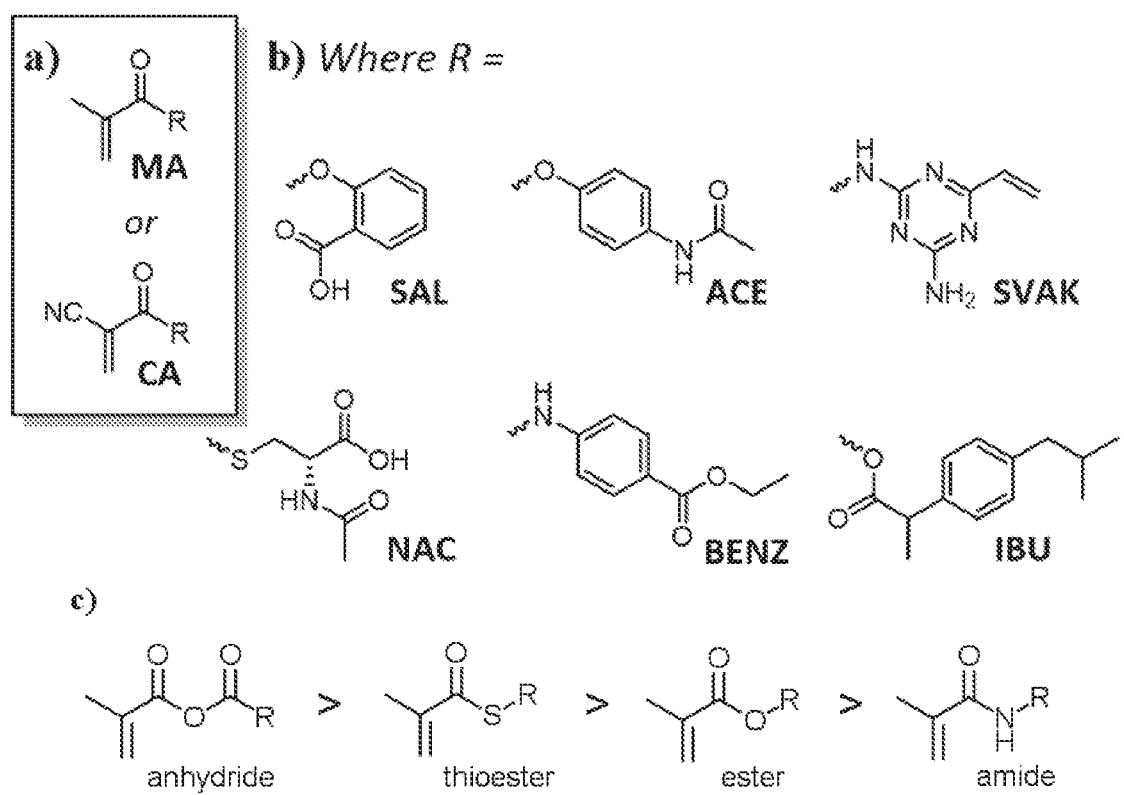
FIG. 1 provides chemical structures of methacrylate or cyanoacrylate backbone of modified monomers, with side groups indicated by "R." b) Therapeutic moieties that may serve as side groups to the acrylate monomers. From top left, side groups depicted are salicylic acid (SAL), acetaminophen (ACE), SVAK-12 (SVAK), N-acetyl-cysteine (NAC), acetylsalicylic acid (ASA), and ibuprofen (IBU). c) representative examples of covalent linkages between the backbone and therapeutic moieties. Chemical bonds are depicted in order of decreasing reactivity to hydrolysis.

In aspects, the monomer has the structure:

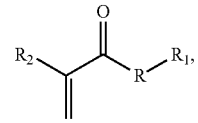

where R is an anhydride bond, a thioester bond, an ester bond, or an amide bond, $R_1$ is a therapeutic agent moiety, and $R_2$ is a cyano or methyl group. In one aspect, when R is ester and $R_2$ is methyl, $R_1$ is not a salicylic acid moiety. Non-limiting examples of therapeutic substituted acrylate monomers are shown in FIG. 1.

Therefore, provided herein are acrylate adhesives that can deliver therapeutic moieties at the site of injury. Currently available topical adhesives include DERMABOND® (2-octylcyanoacrylate, a product of Ethicon), LIQUIBAND® (2-cyanoacrylate-N-butylcyanoacrylate blend, a product of Advanced Medical Solutions), VETBOND™ (N-butylcyanoacrylate, a product of 3M), and TISSUEMEND™ II (methoxypropyl cyanoacrylate-ethyl cyanoacrylate blend, a product of PRN Pharmacal of Pensacola, Fla. (PRN). Octyl cyanoacrylate products display improved flexibility over butyl adhesives, though butyl adhesives have somewhat faster cure times and tend to adhere to tissue surfaces better. The modified acrylate monomers described herein seamlessly integrate with FDA-approved acrylate adhesives, and can therefore be used in place of octyl cyanoacrylate in composite materials to lend flexibility to the adhesive, or as an additive to any existing adhesive product to deliver therapeutics and improve compatibility. Additionally, TISSUEMEND™ is claimed to be absorbable, because its methoxypropyl cyanoacrylate monomers contain labile ester bonds that over time allow the adhesive to degrade. The modified monomers described herein that contain labile covalent linkages will have similar biodegradable/absorbable properties and can therefore fulfill a similar role. This represents an improvement over the TISSUEMEND™ product because the hydrolytic degradation products will be therapeutic, unlike the methoxypropanol released from TISSUEMEND™ products.

In aspects, the compositions and methods described herein aim to address all of the barriers facing the widespread application of acrylate-based adhesives to different wound healing challenges. By incorporating covalent controlled release, compounds described herein deliver therapeutics locally, directly to the wound sites on which they are applied. The use of therapeutics as a side group for acrylate monomers confers enhanced mechanical properties to the cured adhesive and enhanced cytocompatibility to any unreacted monomer. Further, through the choice of covalent tether for the therapeutic and of adhesive composition (for adhesives utilizing a mixture of the proposed monomers and typical adhesive monomers), the degradation profile and mechanism of the adhesive is easily adjusted. Therefore, the materials of the present invention bring sophisticated and novel technology to the field of medical adhesives, providing both convenient closure or fixation and improved, directed healing of wounds.

Therapeutic Agents

Any of a large variety of therapeutic agents may be covalently linked to the acrylate. most therapeutic agents (e.g. drugs, active agents, therapeutic chemical entities) have at least one active group that can be used to link the agent to the acrylate moiety. Certain classes of therapeutic agents may be preferred for inclusion in a medical adhesive as described herein, such as, for example, pain killers, promoters of tissue repair, anti-inflammatory compounds, chemoattractants, and cell adhesion promoting factors.

In one aspect, the therapeutic agent is an analgesic or anesthetic, such as a local anesthetic. Analgesics, including, without limitation, acetaminophen, tramadol or cannabinoids; Non-Steroidal Anti-Inflammatory Drugs (NSAIDs), including, without limitation, bromfenac, colchicine, diclofenac, diflunisal, etodolac, fenoprofen, flurbiprofen, ibuprofen, indomethacin, indoprofen, ketoprofen, ketorolac, meclofenamate, mefenamic acid, meloxicam, nabumetone, naproxen, nepafenac, oxaprozin, phenylbutazone, piroxicam, salicylamide, sulindac, tolmetin; COX-2 Inhibitors including, without limitation, celecoxib, rofecoxib, and etoricoxib; Narcotic Pain Medications (Painkillers) including, without limitation, buprenorphine, butorphanol, codeine, hydrocodone, hydromorphone, levorphanol, meperidine, methadone, morphine, nalbuphine, oxycodone, oxymorphone, pentazocine, propoxyphene, tapentadol; and topical analgesics or anesthetics, including, without limitation, ambucaine, amylocaine, articaine, benzonatate, bupivacaine, butacaine, butanilicaine, chloroprocaine, cinchocaine, cocaine, cuclomethylcaine, dimethocaine, diperodon, benzocaine, dibucaine, lidocaine, oxybuprocaine, butamben, pramoxine, proparacaine, proxymetacaine, tetracaine, meprylcaine, metabutoxycaine, nitracaine, orthocaine, oxetacaine, paraethoxycaine, phenacaine, piperocaine, piridocaine, pramocaine, prilocaine, primacaine, procainamide, procaine, propoxycaine, pyrrocaine, quinisocaine, ropivacaine, tolycaine, trimecaine, tropacocaine, and capsaicin.

In another aspect, the therapeutic agent is a cell fate or reprogramming factor (a cell recruitment agent moiety or a cell programming agent moiety). Compounds that affect the fate of progenitor or stem cells, or that are useful in cellular reprogramming include, without limitation, the following, which are fully described in the art and many of which are commercially-available: PD0325901 and the glycogen synthase kinase-3 (GSK3) inhibitor CHIR99021; Rho-associated coiled-coil-containing protein kinase (ROCK) inhibitors, such as Y-27632 and thiazovivin (Tzv); StemRegenin1 (SR1); the GSK3 inhibitor 6-bromoindirubin-39-oxime (BIO); Valproic acid (VPA); Suberoylanilide hydroxame acid (SAHA); Trichostatin A (TSA); Sodium butyrate (NaB); BIX-01294; RG108; 5-azazcytidine (5-aza); Pamate; Kenpaullone; PD173074; SU5402; A-83-01; SB431542; E-616452; LDN193189; Compound E; JAK Inhibitor I; Pluripotin (SC1); PS48; BayK8644; Forskolin; B105192; AMD3100; diprotin A; dmPGE2; CASIN; kartogenin, P7C3; CHIR99021; SB431542; IDE1; (−) indolactam V, KY02111; IWR-lendo; IWPP2/4; PluriSin #1; BIX-01294; RG108; LY411575; pamate; EPZ004777; 8-Br-cAMP; and PS48 (See, e.g., Zhang, Y, et al. Small molecules, big roles—the chemical manipulation of stem cell fate and somatic cell reprogramming, J. Cell Sci. 2012 125, 5609-5620 and Li, W., et al. Chemical approaches to stem cell biology and therapeutics Cell Stem Cell. 2013 Sep. 5; 13(3): 270-283).

In yet another aspect, the therapeutic agent or R1 is a cell adhesion peptide (e.g., motif or recognition sequence), for example and without limitation: IKVAV (SEQ ID NO: 1); RGD; RGDS (SEQ ID NO: 2); AGD; KQAGDV (SEQ ID NO: 3); VAPGVG (SEQ ID NO: 4); APGVGV (SEQ ID NO: 5); PGVGVA (SEQ ID NO: 6); VAP; GVGVA (SEQ ID NO: 7); VAPG (SEQ ID NO: 8); VGVAPG (SEQ ID NO: 9); VGVA (SEQ ID NO: 10); VAPGV (SEQ ID NO: 11); GVAPGV (SEQ ID NO: 12); and DGEA (SEQ ID NO: 13)). In this case, it is desirable to have the peptide persist in situ on the polyacrylate, so in various aspects, it may be preferable to link the peptide to the acrylate with an amide bond, which can be achieved by linking the N-terminal amine of the peptide with the acrylate.

In aspects, the therapeutic agent is a cytokine or chemoattractant that can be linked to the acrylate moiety as described herein. For example and without limitation, useful therapeutic agents include growth factors, interferons, interleukins, chemokines, monokines, hormones, and angiogenic factors. In certain non-limiting aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, angiopoietin-1 (Ang-1), pleiotrophin protein (neurite growth-promoting factor 1), midkine protein (neurite growth-promoting factor 2), brain-derived neurotrophic factor (BDNF), tumor angiogenesis factor (TAF), cortico-trophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass. As indicated elsewhere herein, polypeptide therapeutic agents can be linked to the acrylate via any active group, such as N-terminal amines, C-terminal carboxyl, internal amines, sulfhydryl, hydroxyl, or carboxyl groups, and active groups may be selectively blocked via any suitable protecting group, as are broadly-known, e.g., Cbz (carbobenzyloxy) or Boc (tert-butyloxycarbonyl) groups for blocking amine groups.

In yet another aspect, the therapeutic agent is an antibiotic, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, and Zn-pyrithione.

In another aspect, the therapeutic agent or R1 is a disease modifying antirheumatic drug (DMARD), such as, without limitation: azathioprine; cyclophosphamide; cyclosporine; hydroxychloroquine; feflunomide; methotrexate; mycophenolate mofetil; sulfasalazine; apremilast; tofacitinib; and/or active metabolites thereof, such as mesalazine, for which sulfasalazine is a prodrug.

Synthesis of Acrylates Having a Therapeutic Side Group.

Acrylates having a therapeutic side group can be prepared in any useful manner, and one of ordinary skill in the art would be able to modify acrylates, such as methacrylates or cyanoacrylates, with therapeutic moieties. Most therapeutic compositions comprise at least one reactive group that can be used to covalently attach the therapeutic composition to produce an anhydride, an ester, a thioester, or an amide bond. For Example, as with the case of AceMA, having an ester linkage between the acetaminophen moiety and the methacrylic moiety in a nucleophilic carbonyl substitution reaction, methacrylic anhydride can be reacted with a hydroxyl group-containing therapeutic agent, to produce the direct ester linkage that, when hydrolyzed, releases the active chemical entity, as with the release of acetaminophen from the methacrylic moiety, for example a (poly)methacrylate backbone formed by the polymerization of the AceMA monomer. In other aspects, amines, such as the N-terminal amine of a peptide, can react with methacrylic acid or cyanoacrylic acid by condensation, or can react with methacrylic anhydride to produce an amide bond. Substituted cyanoacrylates typically require using a Diels Alder reaction to protect the double bond while the carbonyl substitution takes place (see, Basu, A.; et al. PEG-Biscyanoacrylate Crosslinker for Octyl Cyanoacrylate Bioadhesive. *J. Macromol. Rapid Commun.* 2016, 37 (3), 251-256).

In aspects, the therapeutic monomers may be synthesized in a similar pattern.

1. Protect the double bond of the acrylate as needed, typically through a Diels Alder reaction with a labile diene such as anthracene (especially for cyanoacrylates) or furan, which may be useful for creating thioesters of either MAs or CAs.
2. Protect any functional groups that should be preserved in the therapeutic, that will not be used in tethering the therapeutic to the acrylate.
3. Activate the carbonyl of the acrylate. This may take the form of using a commercially available, "pre-activated" acrylate such as methacryloyl chloride, methacrylic anhydride, or methacrylic acid N-hydroxysuccinimide ester. Alternatively, activating reagents such as 1-Ethyl-3-(3-dimethylaminopropyl) carbodiimide (EDC), dicylcohexylcarbodiimide (DCC), thionyl chloride, or oxalyl chloride may be used to activate the acrylate to nucleophilic attack.
4. Select an appropriate combination of solvent and base that will favor nucleophilic attack by the intended functional group of the therapeutic. For example, if a hydroxyl and an amine are present on the same therapeutic, and the hydroxyl group is the desired nucleophile, a base that is strong enough to deprotonate the hydroxyl, but not strong enough to deprotonate the amine may be used. Also, polar protic solvents can favor nucleophilic attack by thiolates more than by alkoxides whereas polar aprotic solvents may make the alkoxide more active as a nucleophile.
5. Combine the activated acrylate and therapeutic, with base, solvent, and catalyst as needed, to create the nucleophilic carbonyl substitution reaction.
6. Purify the product and deprotect the double bond of the acrylate as needed.

According to one aspect or embodiment, the therapeutic agent is linked to a MA or CA moiety and when degraded in situ, the therapeutic agent is released, and thus the monomer linked to the therapeutic agent, and a polymerized product thereof to which the therapeutic agent is linked is deemed a "prodrug". In another aspect, the therapeutic agent is active when in combination with the MA or CA in its polymerized state, and is intended to be retained at the site of the polymer. Thus, the therapeutic agent can be a cell attachment peptide, such as RGD, or other cell adhesion peptides, epitopes, paratopes, haptens, or other binding reagents, such as aptamers. Generally, peptide sequences useful in the described therapeutic monomers are less than 100 amino acids in length, less than 50 amino acids in length, and in aspects, less than 30 amino acids in length. Therapeutic nucleic acids or analogs thereof, such as peptide nucleic acids, such as interfering RNA (RNAi), e.g., small interfering RNA (siRNA), moieties or γ-peptide nucleic acids may also be attached to the acrylate moieties described herein.

Therapeutic Products

According to various aspects of the present invention, therapeutic products are provided, such as a therapeutic adhesive useful, for example, in wound healing, as in repair of wounds as a result of accident, combat, or surgery. The therapeutic monomers or acrylates, and/or polymers thereof, can be used as, for example, an adhesive, filler, drug-delivery composition or device, or coating. In one aspect, the therapeutic product is a composition, such as an adhesive composition, comprising a therapeutic monomer according to any aspect described herein. In one aspect, the composition is a liquid or a dry, reconstitutable liquid that requires addition of a solvent, such as water prior to use. The composition may further include an acrylate adhesive, such as a 2-cyanoacrylate adhesive (also referred to as an alpha cyanoacrylate, such as described in U.S. Pat. No. 5,328,687, among others), such that, when polymerized, the composition forms a copolymer of the therapeutic acrylate and the acrylate adhesive. In one aspect, the acrylate adhesive is one or more of a methacrylate adhesive and a cyanoacrylate adhesive. In another aspect, the acrylate adhesive comprises a $(C_1-C_{12}$ alkyl)-2-cyanoacrylate, which is a compound having the structure:

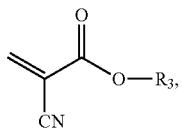

where $R_3$ is a $C_1-C_{12}$ saturated hydrocarbon, and includes branched, unbranched and cyclic structures, or combinations thereof), examples of which include, without limitation: methyl-2-cyanoacrylate, ethyl-2-cyanoacrylate, n-butyl cyanoacrylate, and 2-octyl cyanoacrylate. Adhesive compositions also can include additional compounds or compositions, such as accelerants, initiators (polymerization initiators), polymeric fillers or other nanoparticles, rheology modifiers, radiopaque materials, an free therapeutic agents, e.g., any therapeutic agent as described herein.

The therapeutic adhesive product may comprise up to 100% wt. of one or more type of therapeutic acrylate monomers, for example less than 100% wt. of the therapeutic monomers, such from 0.01% wt. to 90% wt., from 0.1% wt. to 75% wt., or from 1% wt. to 50% wt. of the therapeutic acrylate monomers, and any increment therebetween for all ranges.

In one aspect, a bone cement is provided. Bone cements are generally used not for their adhesive properties, but rely instead on close mechanical interlock between the irregular bone surface(s) and, when present, a prosthesis. A variety of bone cements are available, but a common form is polymethyl methacrylate, which can be provided as two-component materials including a powder (e.g., pre-polymerized PMMA and or PMMA or MMA co-polymer beads or amorphous powder, and also often including a radio-opacifer (radiopaque, e.g., ZrO2 or BaSO4), a polymerization initiator (e.g. di-benzoyl peroxide) and an accelerator (e.g., N, N-dimethyl-p-toluidine (DmpT)) and a liquid acrylate monomer, often including a stabilizer (e.g. hydroxyquinone). The two components are mixed and polymerized by an free radical polymerization process.

In one aspect, a bone cement is provided that comprises two components: a powder acrylate polymer composition, and a liquid acrylate adhesive composition. Either or both of the powder acrylate polymer and the liquid acrylate adhesive may comprise therapeutic monomer residues or therapeutic monomers, respectively, according to any aspect as described herein.

In a further aspect, a kit is provided, comprising at least one vessel comprising a therapeutic monomer according to any aspect herein, or a polymer comprising therapeutic monomer residues of those therapeutic monomers. For example, a vessel, such as a dropper bottle or a medical syringe is provided, comprising within the dropper bottle or syringe a composition comprising an adhesive composition comprising a therapeutic acrylate monomer according to any aspect described herein. Additional ingredients can be included in the kit either mixed with the therapeutic acrylate monomer, or in a separate container or vessel, such as a non-therapeutic adhesive to co-polymerize with the therapeutic monomer, such as a pharmaceutically-acceptable adhesive, accelerants, initiators, stabilizers, or any other ingredients useful in the preparation or delivery of a therapeutic acrylate adhesive, including containers or vessels and tools useful in the preparation and delivery of the adhesive.

In one aspect, a bone cement kit is provided, comprising a first vessel containing at least the powdered acrylate polymer composition, and a second vessel containing at least a liquid or dry-reconstitutable acrylate adhesive, one or both of the vessels include therapeutic acrylate monomers as described herein. In one aspect, the powder acrylate polymer in the first vessel may comprise one or more therapeutic acrylate monomer residues, according to any aspect as described herein. In another aspect, the liquid or dry-reconstitutable acrylate adhesive in the second vessel may comprise one or more therapeutic acrylic monomers, according to any aspect as described herein. In another aspect, the powder acrylate polymer in the first vessel the liquid comprises one or more therapeutic acrylic monomer residues and the liquid or dry-reconstitutable acrylate adhesive in the second vessel comprises one or more therapeutic acrylic monomers, according to any aspect as described herein, wherein the therapeutic acrylic monomers of the one or more therapeutic acrylic monomer residues of the powder acrylate polymer of the first vessel is the same as or different from the one or more therapeutic acrylic monomers of the liquid or dry-reconstitutable acrylate adhesive in the second vessel. Stabilizer(s), initiator(s), accelerant(s), radiopaque compound(s), or any other desirable ingredient may also be included within the first or second vessel as appropriate, or in one or more additional vessels. For any kit described herein, suitable packaging, such as containers, pouches or wrappers, instructions or other indicia, mixing vessels, mixing devices, mixing utensils, tubing, bone cement deposition tools such as a medical syringe or a clutch-handle cement delivery device (see, e.g., DURO-JECT® Bone Cement injector set, from Cook Medical of Bloomington Ind., or OSSEOPERM® bone cement kit from Aegis Spine of Santa Rosa, Calif.), etc. may also be included in the kit.

In one aspect of the present invention, the liquid and/or polymerized powder component of acrylate-based bone cements, include an acrylate monomer as described herein, that includes at least one bone-healing or osteogenic therapeutic agent moieties, such as salicylate, SVAK-12, or N-acetyl cysteine, or any combination thereof. For example, the polymeric powder may be a homopolymer, comprising up to 100% wt. of therapeutic acrylate monomers (monomer residues), e.g., comprising bone-healing or osteogenic therapeutic agent moieties, such as salicylate, SVAK-12, or N-acetyl cysteine, or any combination thereof. In aspects, the polymeric powder may be a copolymer comprising less than 100% wt. of the therapeutic monomers, such from 0.01% wt. to 90% wt., from 0.1% wt. to 75% wt., or from 1% wt. to 50% wt. of the therapeutic acrylate monomers, and any increment therebetween for all ranges. with the remainder of monomer residues in the copolymer being acrylate moieties that are not substituted with the therapeutic agent. Likewise, the liquid component of the bone cement may comprise up to 100% wt. of therapeutic monomers, e.g., comprising bone-healing or osteogenic therapeutic agent moieties, such as salicylate, SVAK-12, or N-acetyl cysteine, or any combination thereof. In aspects, the liquid may comprise less than 100% wt. of the therapeutic monomers, such from 0.01% wt. to 90% wt., from 0.1% wt. to 75% wt., or from 1% wt. to 50% wt. of the therapeutic acrylate monomers, and any increment therebetween for all ranges. with the remainder being acrylate moieties that are not substituted with the therapeutic agent. Monomers comprising other therapeutic agents may be included in either the powder or liquid component of the bone cement, such as monomers comprising, for example and without limitation, antibiotics, cell-adhesion moieties/peptides (e.g., DGEA (SEQ ID NO: 13)), analgesics, or anesthetics.

In the Examples, below, "TMA-MMA adhesives" refers to adhesives in which the Therapeutic Methacrylic (TMA) monomer, benzoyl peroxide (BPO) initiator, and dimethyl-p-toluidene (DMPT) accelerator are dissolved in methyl methacrylate (MMA).

"TMA-BCA adhesives" refers to adhesives in which the Therapeutic Methacrylic (TMA) monomer, BPO, and DMPT are dissolved in butyl cyanoacrylate (BCA). For example, Vetbond™ was used as the source of BCA for these adhesives in the Examples, below.

Example 1: "IbuMA," Liquid Sutures for Cutaneous Repair; Rapid Therapeutic Release A compound was prepared comprising methacrylate (MA) and ibuprofen (IBU), joined by an anhydride bond. The compound is made by combining ibuprofen (13 mmol, 3 g) and MEHQ (20 mg) in a Schlenk flask under argon. The flask is placed in a cool water bath (15° C.) and methacryloyl chloride (10 mmol, 1 mL) is added by syringe. The reaction is stirred vigorously for 2 h. Dry hexanes (50 mL) is then added by cannula, followed by a second fraction of ibuprofen (1 g) added in one shot. The reaction is allowed to warm slowly to room temperature and is stirred for an additional 4 days. The slurry is passed through a column of activated neutral alumina under inert gas to filter out salts and remove traces of moisture. Solvent is then removed under high vacuum to yield a clear, free-flowing oil.

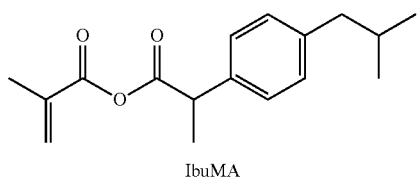 [SMILES: C=C(C)C(=O)OC(=O)C(C)c1ccc(CC(C)C)cc1]

IbuMA

Following surgical procedures, patients frequently complain of pain once procedural anesthetics wear off. For this post-operative period, patients are often prescribed non-steroidal anti-inflammatory drugs (NSAIDs) to ease their suffering. However, patient compliance, especially in children, can be problematic. Further, though cheap, and non-habit forming, NSAIDs are associated with increased risk of gastrointestinal distress (including ulceration and bleeding), hepatic dysfunction, and heart attacks, especially when used for prolonged periods of time. Thus, a cement or liquid suture that could elute a pain-relieving therapeutic at critical time points following procedures would be convenient and advantageous to avoiding patient non-compliance, complications due to overdose, and/or systemic side effects. To this end, we have synthesized IbuMA, which has the ability to deliver ibuprofen from a cured adhesive in the hours to days following application.

IbuMA is a liquid monomer at room temperature, and therefore may be used pure, or as part of a composite adhesive. IbuMA is soluble in commercial formulations of both n-butyl cyanoacrylate and methyl methacrylate monomer. The effectiveness of IbuMA as an additive to enhance current commercial adhesives has been characterized for a composite adhesive containing 10% IbuMA by weight, 5% of a radical initiator-accelerator system, and 85% n-butyl cyanoacrylate (BCA, obtained in the form of the 3M tissue adhesive VETBOND™). Such composite compositions would be useful as topical skin adhesives for apposing and securing lacerated cutaneous tissue. The tested composition has demonstrated controlled release of an appropriate dose of ibuprofen, decreased release of the toxic formaldehyde degradation product, improved cytocompatibility, and effective adhesion to porcine skin in an ex vivo wound closure model.

Figure 2A:
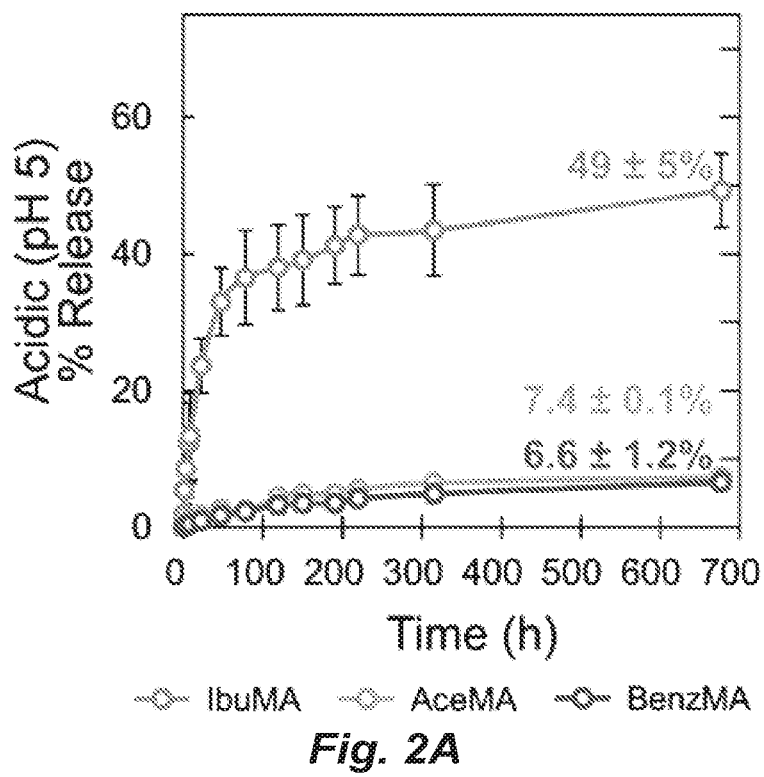
FIG. 2. Covalent controlled release of ibuprofen (from IbuMA-BCA), acetaminophen (from AceMA-BCA), or benzocaine (from BenzMA-BCA) in A) acidic (pH 4.9 sodium acetate buffer) and B) neutral (pH 7 deionized water) conditions. Percent release represents the amount of therapeutic detected in the supernatant above submerged adhesives divided by equivalents of therapeutic carried in the TMA-BCA adhesive. Values at the right indicate percent release at last indicated time point. In acidic conditions, the rate constants of release from IbuMA-BCA, AceMA-BCA, and BenzMA-BCA adhesives, determined using data collected between 0 and 7 h, were found to be statistically different ($1300 \pm 700$, $110 \pm 30$, and $40 \pm 10$ $M^{-1}$ $h^{-1}$, respectively).
Figure 2B:
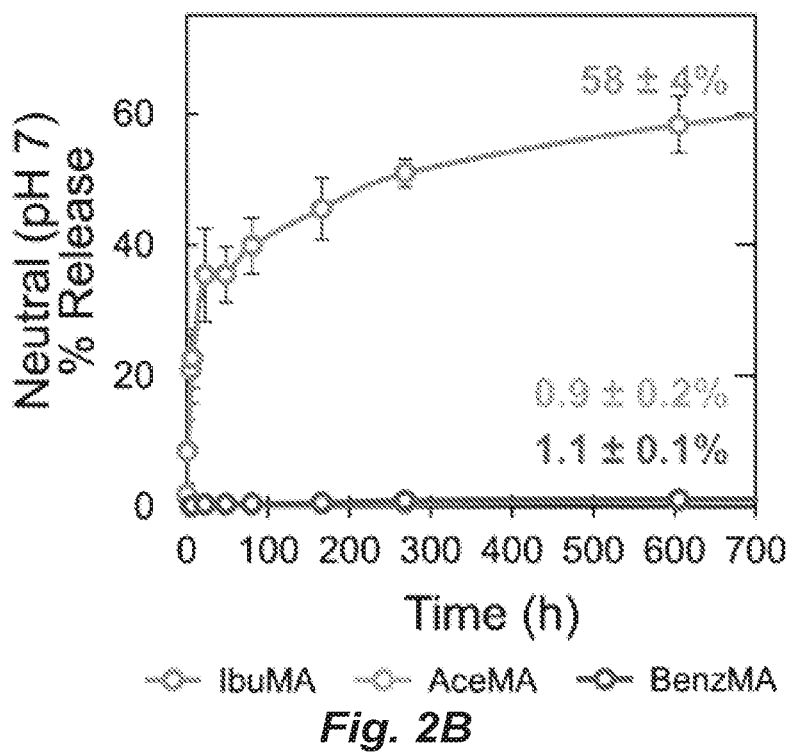
Figure 3:
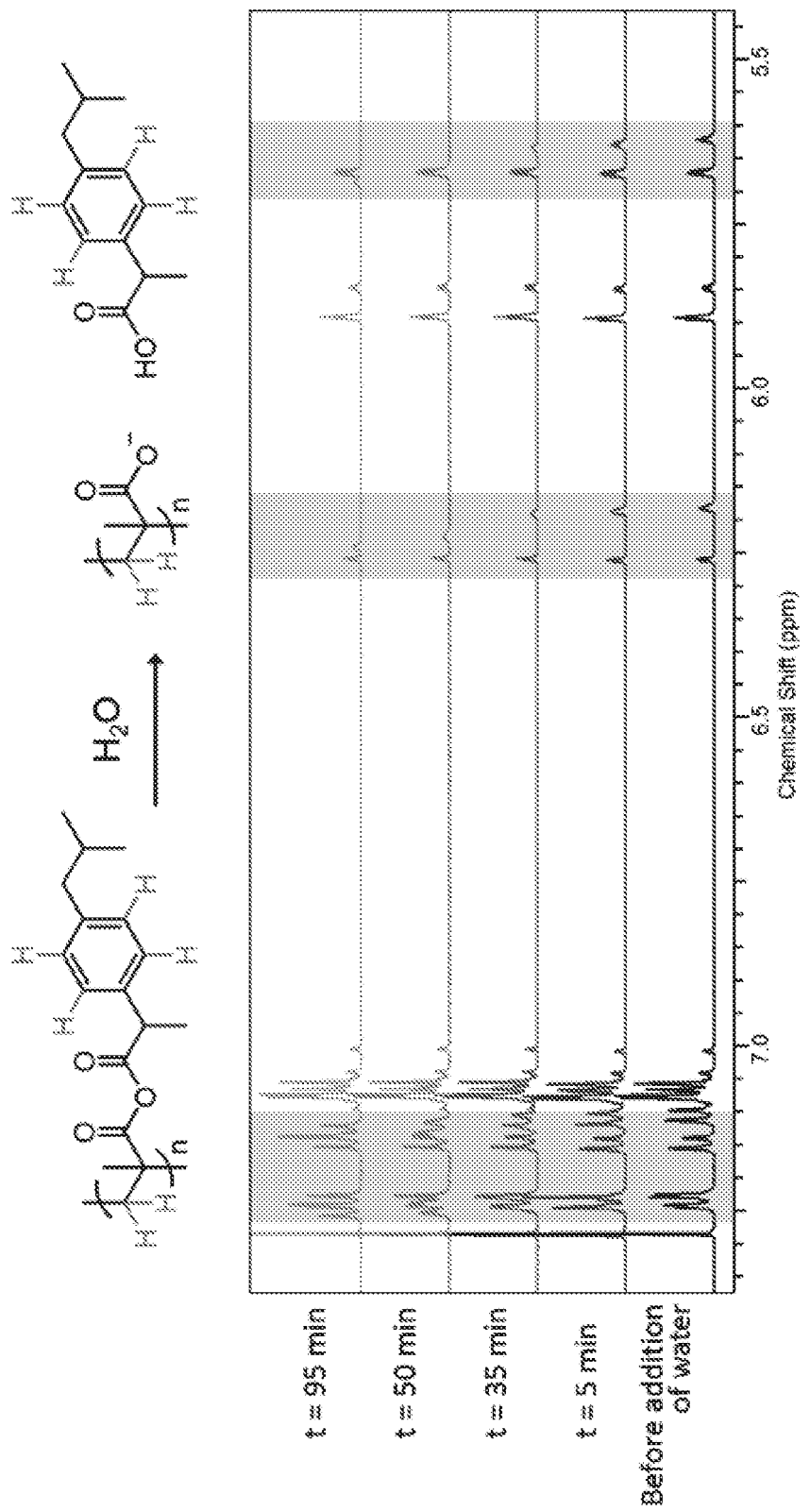
FIG. 3 provides a demonstration of the reaction of oligo-IbuMA (dissolved in 90 μL $CDCl_3$) with $D_2O$ (10 μL) as observed by $^1H$ NMR (500 MHz). "Oligo-IbuMA" represents the mixture of IbuMA monomer, short-chained IbuMA oligomers containing a variety of end groups, and partially hydrolyzed IbuMA that is obtained upon exposure of IbuMA monomer to moist/ambient air. Over time following exposure to $D_2O$, the multiplets describing the mixture of IbuMA derivatives at t=0 are seen to converge, especially in the aromatic (blue) and vinylic (red) regions, suggesting a homogenization of the IbuMA mixture through hydrolysis of the ibuprofen side group.
Figure 4:
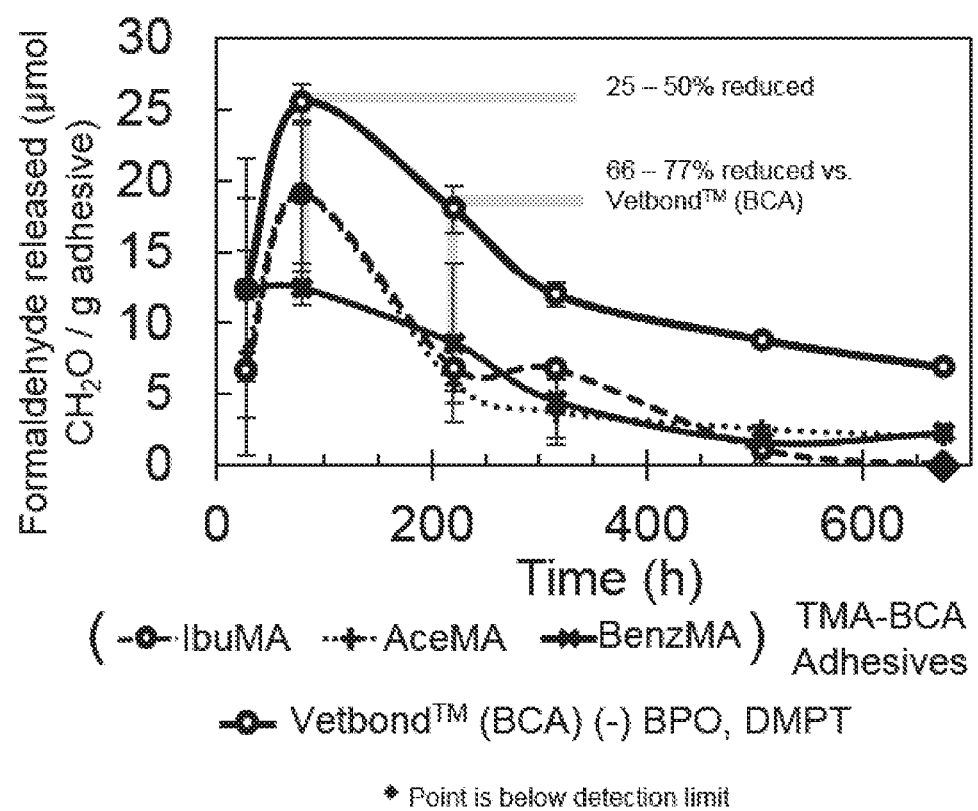
FIG. 4. Amount of formaldehyde detected in the supernatant above TMA-BCA adhesives submerged in deionized, degassed water over the course of four weeks (675.5 h), normalized per gram of adhesive, detected via fluorometric assay utilizing the reaction between formaldehyde, acetoacetanlilide, and ammonia that produces fluorescence (excitation 370/20 nm, emission 470/20 nm). The amount of formaldehyde detected in the presence of TMA-BCA adhesives is consistently lower compared to Vetbond™ alone.
Figure 5:
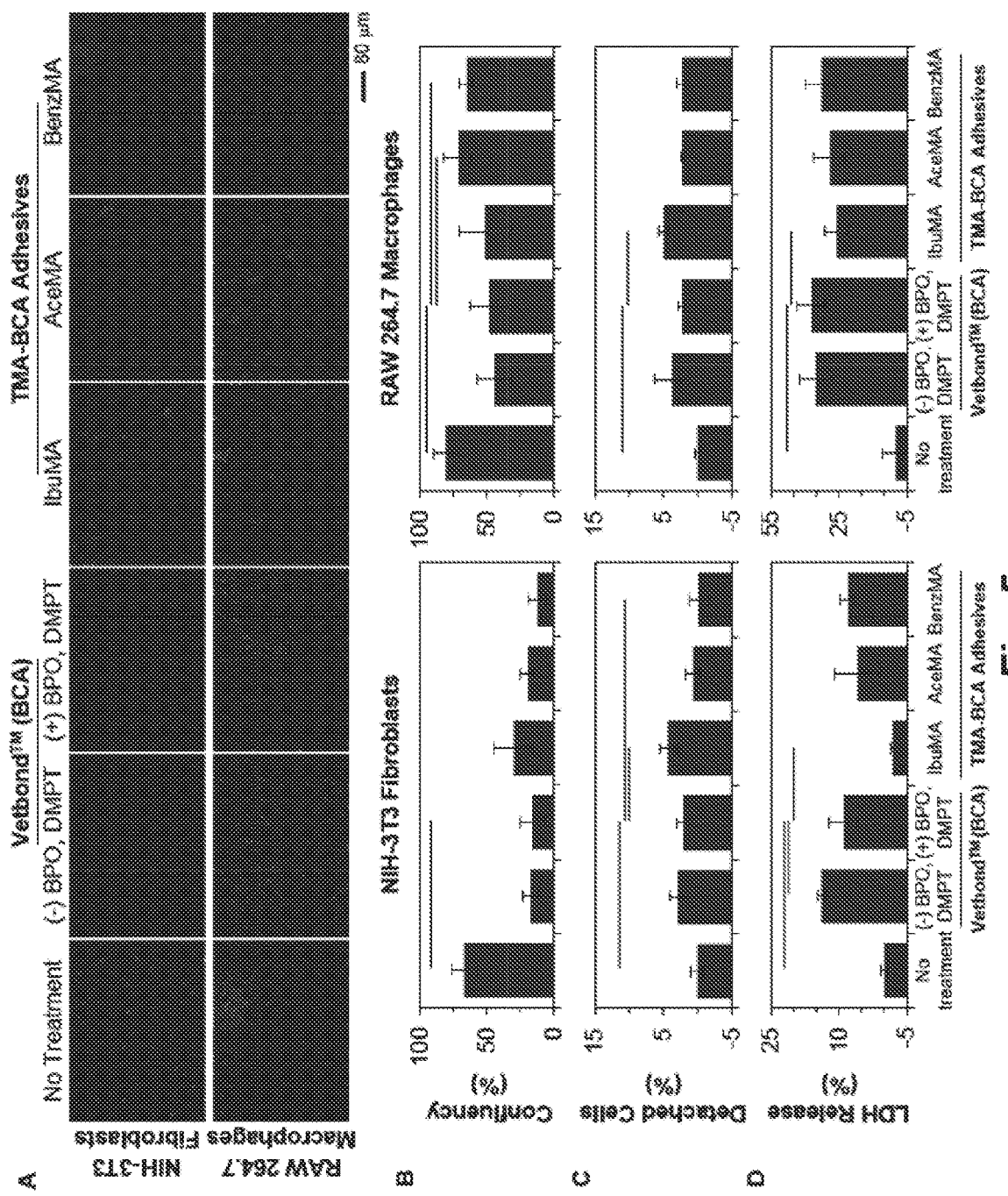
FIG. 5 Cytocompatibility of TMA-BCA adhesives cured in situ in the cell culture media above NIH-3T3 fibroblasts and RAW 264.7 macrophages. A) Representative fluorescence microscopy images of cellular nuclei labeled with Hoechst 33342, systematically cropped from the center section of whole-well images. Adhesives were retained in wells during imaging so as not to disturb cells; images show uneven background due to signal from the adhesives, but distinct nuclei. B) Cellular confluency was quantified from whole-well images to reduce uncertainty caused by uneven background and cell density. C) Quantification of cells that have detached from the substrate, feature scaled to the positive and negative controls. D) Cytotoxicity assessed by LDH release, feature scaled to the positive and negative controls. Note that lines indicate significant differences compared to cells exposed to Vetbond™ (+) BPO, DMPT.

The IbuMA-BCA composite adhesive demonstrates a burst release profile, releasing a clinically relevant amount of therapeutic in the hours after application, which tapers off after approximately 4 days (FIGS. 2A and 2B). One gram of 10% IbuMA adhesive, expected to cover the surface of a small laceration, will therefore release 12+−6 mg ibuprofen in the first 3.4 hours after application, which is on the same order of magnitude and time scale as currently available topical ibuprofen medications. Because ibuprofen has been covalently bonded to the methacrylate backbone, hydrolysis of ibuprofen from IbuMA upon exposure to water can be confirmed by $^1$H-NMR (FIG. 3). Compared to VETBOND™ (the BCA-only control), the IbuMA-BCA composite adhesive showed a 35% reduction in formaldehyde release at 79 h after being submerged in water, and a 66% reduction in formaldehyde release at 220 h (FIG. 4). The decrease in formaldehyde production has been correlated to an improvement in cytocompatibility. When a drop of adhesive was cured in situ in the cell culture media above NIH-3T3 fibroblasts, a cell type found in cutaneous tissue, IbuMA-BCA showed greater cell proliferation (as measured by cell confluency after 24 h of exposure) and significantly fewer dead cells (by a student's t-test with $p<0.05$) than VETBOND™ (FIG. 5). Furthermore, the IbuMA-BCA adhesive demonstrated comparable adhesion to porcine skin versus VETBOND™, with no significant reduction in peak load or stress at failure (FIG. 6). The shear modulus, an indication of stiffness, of IbuMA-BCA (0.6±0.4 MPa) demonstrates better mechanical match with porcine skin (measured by Shergold, O. A., et al. (The Uniaxial Stress versus Strain Response of Pig Skin and Silicone Rubber at Low and High Strain Rates. Int. J. Impact Eng. 2006, 32 (9), 1384) to be 1.5 MPa) than VETBOND™ (3.9±2.2 MPa) (FIG. 7). Further details are provided in Example 5, below.

Example 2: "BenzMA," Liquid Sutures for Cutaneous Repair; Extended Therapeutic Release A compound was prepared comprising methacrylate (MA) and benzocaine (BENZ), joined by an amide bond. The compound is made by first dissolving benzocaine (1.67 g, 10 mmol) and MEHQ (20 mg) in dry chloroform (150 mL) and cooling on an ice bath. $K_2CO_3$ (2.4 g, 17 mmol) is added in one shot, followed by methacryloyl chloride (1.0 mL, 10 mmol), added dropwise via syringe over five minutes. The reaction is warmed slowly to room temperature and stirred for 5 h. Solids are removed by filtration, and the organic solution is washed (1× water, 3×5% aqueous HCl, 2× water) and dried over $MgSO_4$. The solution is filtered and concentrated under vacuum. The crude product is purified by passing through a silica plug using a 4:1 mixture of chloroform: ethyl acetate as eluent. The solvent is removed under vacuum to give an off-white solid.

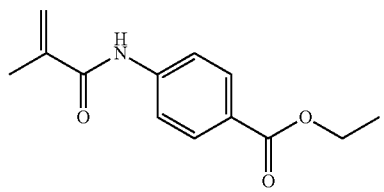

BenzMA

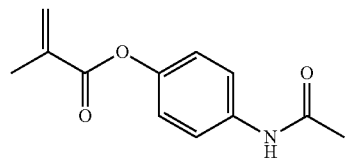

AceMA

Following surgical procedures, sustained pain relief that extends into the weeks following the procedure may be desirable under certain circumstances. To this end, BenzMA was synthesized, utilizing an amide tether that will undergo hydrolysis at a significantly slower rate than the anhydride bond tether used in the IbuMA, described in Example 1. The effectiveness of BenzMA as an additive to enhance current commercial adhesives was characterized for a composite adhesive containing 10% BenzMA by weight, 5% of a radical initiator-accelerator system, and 85% n-butyl cyanoacrylate (BCA, as VETBOND™). This composition, referred to henceforth as BenzMA-BCA, would also be appropriate as a topical skin adhesive for apposing and securing lacerated cutaneous tissue.

Comparison of BenzMA-BCA and IbuMA-BCA composite adhesives demonstrates the range of therapeutic release characteristics and mechanical properties that can be achieved through the design of the present invention. Like IbuMA-BCA, BenzMA-BCA demonstrates decreased formaldehyde release (FIG. 4) and improved cytocompatibility for both NIH-3T3 fibroblasts and RAW264.7 macrophages (FIG. 5) compared to VETBOND™. Of note, the BenzMA-BCA adhesive has shown significantly improved adhesive properties compared to VETBOND™ for both aluminum lap shear (FIG. 8) and porcine skin (FIG. 6) adhesive tests, including a 219% increase in toughness for aluminum lap shear experiments. Further details are provided in Example 5, below.

Example 3: "AceMA," Liquid Sutures for Cutaneous Repair; Intermediate Therapeutic Release A compound was prepared comprising methacrylate (MA) and acetaminophen (ACE), joined by an ester bond. The compound is made by combining acetaminophen (1.51 g, 10 mmol) and dimethylaminopyridine (DMAP, 0.098 g) with dry chloroform (25 mL) in a flame-dried 50 mL roundbottom flask under argon. Triethylamine (TEA, 1.66 mL, 12 mmol) is added by syringe, and the flask placed on ice. Methacrylic anhydride (1.49 mL, 10 mmol) is added dropwise by syringe over several minutes. The reaction is then allowed to warm to room temperature and stirred overnight before being washed with 3N HCl (4×25 mL) followed by saturated NaHCO₃ (1×25 mL). The organic layer is dried over MgSO₄ for several hours before being filtered. The solvent is removed under vacuum to yield a white powdery solid.

AceMA was synthesized to demonstrate properties that are intermediate to the IbuMA, described in Example 1, and BenzMA, described in Example 2. AceMA serves as an example of how the described compositions may be tuned to suite intermediate pain relief cases. The effectiveness of AceMA as an additive to enhance current commercial adhesives has been characterized for a composite adhesive containing 10% AceMA by weight, 5% of a radical initiator-accelerator system, and 85% n-butyl cyanoacrylate (BCA, as VETBOND™). This composition is referred to as AceMA-BCA, and would also be appropriate as a topical skin adhesive for apposing and securing lacerated cutaneous tissue.

Like IbuMA-BCA and BenzMA-BCA, AceMA-BCA also demonstrates decreased formaldehyde release (FIG. 4) and improved cytocompatibility (FIG. 5) compared to VETBOND™. At pH 4.9, which mimics that of skin and healing wounds, AceMA-BCA shows an intermediate sustained release of acetaminophen over the course of 300 h (FIG. 2), consistent with the time scale of ester bond hydrolysis in similarly acidic conditions. Also, AceMA-BCA demonstrated increased stiffness over VETBOND™ (FIG. 7), which can be a useful tool in engineering hard-soft tissue interfaces by enabling access to materials with a variety of mechanical properties. Further details are provided in Example 5, below.

Example 4: Bone Cement

"SAL-MA":

A compound was prepared comprising methacrylate (MA) and salicylic acid (SAL), joined by either an anhydride bond or an ester bond. The compound is made by combining salicylic acid (10 mmol) and dimethylaminopyridine (DMAP, 0.098 g) with dry chloroform (25 mL) in a flame-dried 50 mL roundbottom flask under argon. Triethylamine (TEA, 1.66 mL, 12 mmol) is added by syringe, and the flask placed on ice. Methacrylic anhydride (1.49 mL, 10 mmol) is added dropwise by syringe over several minutes. The reaction is then allowed to warm to room temperature and stirred overnight before being washed with 3N HCl (4×25 mL). The organic layer is dried over MgSO₄ for several hours before being filtered and reduced to a minimum volume under vacuum. The crude product is then passed through a column of silica using an eluent of 8:2 PET ether and diethyl ether, and the solvent is removed under vacuum to yield a white powdery solid. The anhydride bond compound can be made by using a weaker base to selectively deprotonate the carboxylic acid instead of the hydroxyl group of SAL, and a more strongly activated methacrylate such as methacryloyl chloride.

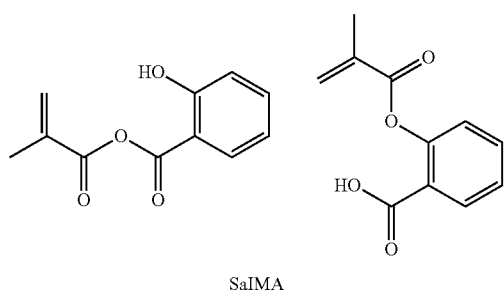

SalMA

It has been shown that salicylic acid (SAL) can promote bone healing. Further, SAL is often taken orally to mitigate pain from traumatic injury or surgery, as well as to prevent the formation of blood clots following surgical procedures. SAL contains both hydroxyl and carboxylic acid groups, so SAL can be tethered to MA through two different chemical bonds (ester and anhydride, respectively). An adhesive containing SAL-MA monomers with a blend of these two covalent bonds would provide highly tunable control over release kinetics, according to the blend composition. When incorporated into traditional bone cement, SAL-MA can mitigate pain following traumatic bone injury, provide sustained pain relief following corrective surgical procedures, and enhance bone healing.

"SVAK-MA": Compounds were prepared comprising one or two methacrylate (MA) moieties and SVAK-12 (SVAK), joined by an amide bond. The compound is made by combining SVAK-12 (0.14 g, 1 mmol) and MEHQ (10 mg) in dry dimethylformamide (6 mL) under nitrogen. The flask is placed on an ice bath. Methacryloyl chloride (0.1 mL, 1 mmol) is added dropwise by syringe over a period of ten minutes. The reaction is allowed to warm to room temperature and stirred several hours. The product is precipitated from the reaction mixture by addition to diethyl ether (70 mL). The suspension is centrifuged, the supernatant is decanted off, and the solid pellet is washed 2× more with diethyl ether. After decanting the final supernatant, the solid is dried under vacuum.

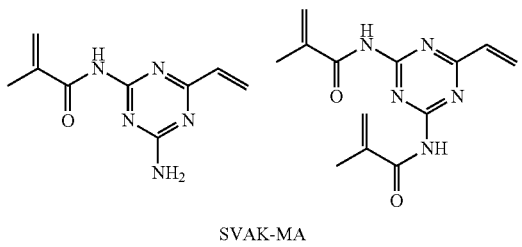

SVAK-MA

SVAK-12 is a synthetic small molecule known to enhance the potency of BMP-2, which in turn promotes osteogenesis (Wong, E., et al. A Novel Low-Molecular-Weight Compound Enhances Ectopic Bone Formation and Fracture Repair. *J. Bone Joint Surg. Am.* 2013, 95 (5), 454). Following critical injury to bone, the most common source of failure of therapeutic implants is poor cell adhesion at the bone-implant interface. Incorporation of SVAK-12 into bone cement can improve the bone-implant interface by encouraging growth and infiltration of osteoblastic cells into nooks at the interface of the implant. Because diffusion of SVAK-12 away from the site of bone injury is undesirable, an amide bond can be used as a robust linker to anchor SVAK-12 to the MA resin. Thus, the SVAK-MA bone cement will sustain its therapeutic activity throughout the healing process.

"NAC-MA": Compounds were prepared comprising a methacrylate (MA) moiety and N-acetyl cysteine (NAC), joined by either a thioester or anhydride bond. The compound is made by first protecting the double bond of the acrylate moiety using a Diels Alder reaction. Then, the carbonyl of the acrylate moiety is activated toward nucleophilic attack by either the thiol or the carboxylate group of NAC, which will create either the thioester or the anhydride tethered NAC-MA, respectively. In the case of the thioester tether, thiolates are better nucleophiles than carboxylates and so will out-compete the carboxylate in the nucleophilic carbonyl substitution reaction that creates the thioester NAC-MA. In the case of the anhydride tether, the thiol group can be protected by formation of a disulfide bond prior to the nucleophilic carbonyl substitution reaction. Then, following the nucleophilic carbonyl substitution, the protecting groups can be removed by a Retro Diels Alder to reveal the acrylate double bond and, if necessary, a reductive cleavage of the disulfide bond to reveal the free thiol.

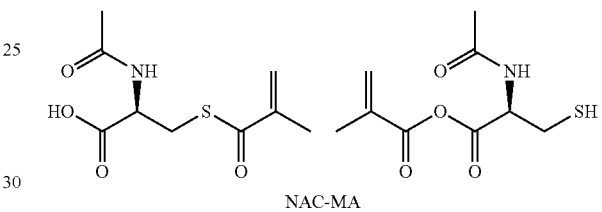

NAC-MA

N-acetyl cysteine (NAC), an amino acid derivative, has been found to enhance osteogenesis by inducing osteoblastic differentiation. Further, NAC has been shown to protect osteoblastic function in healthy bone cells from oxidative stress, such as that caused during the polymerization of MA cements. NAC is therefore an excellent candidate for therapeutic bone adhesives. NAC can be tethered to MA by either an anhydride or a thiol ester bond. Acrylate resins can leech significant amounts of unreacted monomer in the hours following application. An anhydride linkage would provide immediate protection to existing cells from unreacted monomer in the minutes to hours following application of the adhesive. A thiol ester linkage would be expected to be somewhat more reactive to hydrolysis than a typical ester linkage; therefore, this type of covalent bond would be useful for stimulating osteogenesis in the days to weeks following application, thus helping to accelerate the early stages of wound healing. A composite adhesive containing a certain mixture of the two covalent linkages provides a tunable release profile.

Example 5—Covalently Controlled Drug Delivery Via Therapeutic Methacrylic Tissue Adhesives Materials Methacryloyl chloride, dimethylaminopyridine, potassium carbonate, formaldehyde (37% w/w aq. stabilized with methanol), and acetoacetanilide were obtained from Alfa Aesar. Methacrylic anhydride, acetaminophen, benzocaine, triethylamine, benzoyl peroxide (BPO), anhydrous magnesium sulfate, ammonium acetate, and dimethyl sulfoxide were obtained from Sigma Aldrich. 4-methoxyphenol (MEHQ) was obtained from Fluka. N,N-dimethyl-p-toluidine (DMPT) was obtained from TCI America. Hydrochloric acid (ACS plus grade) and sodium bicarbonate were obtained from Fischer Scientific. Vetbond™ was obtained from 3M. These reagents were used as received. Ibuprofen sodium salt (Fluka Analytical) was dried under high vacuum at 90° C. and stored in a 120° C. oven between uses. Solvents including hexanes, dichloromethane, and chloroform were obtained from EMD Millipore, dried over 3 Å molecular sieves, degassed with argon, and passed through a column of activated neutral alumina to dry directly prior to use. NMR solvents were purchased from Cambridge Isotope Laboratories, Inc. unless otherwise stated. All reagents used for cell culture were purchased from ThermoFisher Scientific, with the exception of Calcein AM, which was purchased from PromoKine.

Instrumentation for Monomer Characterization.

Monomers were characterized by $^1$H NMR (Bruker Avance AV300) and $^{13}$C NMR (Bruker Avance III 500) spectroscopy as solutions in $CDCl_3$, Attenuated Total Reflectance Fourier Transform Infrared (ATR FT-IR) spectroscopy (Perkin Elmer Frontier with a Germanium crystal, 4 $cm^{-1}$ resolution from 700-4000 $cm^{-1}$) neat, and Gas Chromatography Mass Spectrometry with Electron Ionization (GC-MS) (Hewlett-Packard Agilent 6890-5973 GC-MS workstation, with a Hewlett-Packard fused silica capillary column crosslinked with 5% phenylmethylsiloxane, injection temperature 250° C., program temperature from 70 to 280° C. at 10° C./min) as solutions in diethyl ether. For GC-MS, the five most abundant m/z are reported. Melting points were determined by Differential Scanning Calorimetry (Perkin Elmer DSC 4000) and are reported as average±standard deviation.

Synthesis

Ibuprofen Methacrylic Anhydride (IbuMA).

Ibuprofen (13 mmol, 3 g) and MEHQ (20 mg) were combined in a Schlenk flask under argon, and placed in a cool water bath (15° C.). Methacryloyl chloride (10 mmol, 1 mL) was added by syringe. The reaction was stirred vigorously for 2 h. Dry hexanes (50 mL) was added by cannula, followed by a second fraction of ibuprofen (1 g) added in one shot. The reaction warmed slowly to room temperature and was stirred for an additional 4 days. The slurry was passed through a column of activated neutral alumina under inert gas to filter out salts and remove traces of moisture. Solvent was then removed under high vacuum to yield a clear, free-flowing oil (2.2 g, 80%). mp (by DSC): −69±7° C. $^1$H NMR (300 MHz, $CDCl_3$) δ 7.24 (d, J=7.50 Hz, 2H), 7.10 (d, J=7.50 Hz, 2H), 6.14 (s, 1H), 5.57 (s, 1H), 3.68 (q, J=7.17 Hz, 1H), 2.48 (d, J=7.19 Hz, 2H), 1.91 (s, 3H), 1.89 (m, J=6.65 Hz, 1H), 1.47 (d, J=7.19 Hz, 3H), 0.94 (d, J=6.65 Hz, 6H). $^{13}$C NMR (126 MHz, CDCl3) δ: 170.1, 163.0, 141.2, 136.3, 135.8, 129.7, 129.2, 127.4, 46.1, 45.2, 30.2, 22.5, 17.8. ATR-IR (neat, $cm^{-1}$): v=2960 m (C—H), 1804 s (anhydride C=O), 1734 s (anhydride C=O), 1510 m (aromatic), 1456 m (aromatic), 1030 s (anhydride C—O), 948, 850, 798.

Acetaminophen Methacrylate (AceMA).

AceMA was synthesized according to the procedure described by Licea-Claverie et al. (A. Licea-Claverie, E. Rogel-Hernandez, J. A. Lopez-Sanchez and L. A. Castillo-Arambula, Des. Monomers Polym., 2003, 6, 67-80) for the synthesis of carboxylaryl methacrylates using methacrylic anhydride, triethyl amine, and catalytic dimethylaminopyridine. Briefly, a flame-dried 50 mL roundbottom flask under argon was charged with dry chloroform (25 mL). Acetaminophen (1.51 g, 10 mmol) and DMAP (0.098 g) were added in one shot. TEA (1.66 mL, 12 mmol) was added by syringe, and the flask placed on ice. Methacrylic anhydride (1.49 mL, 10 mmol) was added dropwise by syringe over several minutes. The reaction was then allowed to warm to room temperature and stirred overnight before being washed with 3N HCl (4×25 mL) followed by saturated $NaHCO_3$ (1×25 mL). The organic layer was dried over $MgSO_4$ for several hours before being filtered. The solvent was removed under vacuum to yield a white powdery solid. The reaction yielded a white powdery solid (1.5 g, 70%). mp (by DSC): 122±2° C. $^1$H NMR (300 MHz, $CDCl_3$) δ 7.51 (d, J=8.86 Hz, 2H), 7.42 (br, 1H), 7.07 (d, J=8.86 Hz, 2H), 6.36 (s, 1H), 5.78 (s, 1H), 2.18 (s, 3H), 2.08 (s, 3H). $^{13}$C NMR (126 MHz, CDCl3) δ: 169.3, 166.4, 146.9, 136.1, 135.8, 127.7, 121.7, 121.2, 24.0, 18.3. ATR-IR (neat, $cm^{-1}$): v=3310 m (secondary amide N—H), 3070 w (Ar—H), 1731 s (ester C=O), 1664 s (amide I), 1608 m (amide II), 1510 s (aromatic), 1200 s (ester C—O), 1130 s (ester C—O), 1023, 944, 884, 820, 725. GC-MS (EI): m/z 161 (100%), 203 (59), 218 ([M-H]$^+$, 49), 175 (46), 69 (37).

Benzocaine Methacrylamide (BenzMA).

BenzMA was synthesized as follows: benzocaine (1.67 g, 10 mmol) and MEHQ (20 mg) were dissolved in dry chloroform (150 mL) and placed on ice. $K_2CO_3$ (2.4 g, 17 mmol) was added in one shot, followed by methacryloyl chloride (1.0 mL, 10 mmol), added dropwise via syringe over five minutes. The reaction was warmed slowly to room temperature and stirred for 5 h. Solids were removed by filtration, and the organic solution was washed (1× water, 3×5% aqueous HCl, 2× water) and dried over $MgSO_4$. The solution was filtered and concentrated under vacuum. The crude product was purified by passing through a silica plug using a 4:1 mixture of chloroform: ethyl acetate as eluent. The solvent was removed under vacuum to give an off-white solid (1.8 g, 75%). mp (by DSC): 98.5±0.7° C. $^1$H NMR (300 MHz, $CDCl_3$) δ 8.03 (d, J=8.66, 2H), 7.97 (br, 1H), 7.68 (d, J=8.66, 2H), 5.84 (s, 1H), 5.51 (s, 1H), 4.38 (q, J=7.15 Hz, 2H), 2.07 (s, 3H), 1.40 (t, J=7.15, 3H). $^{13}$C NMR (126 MHz, CDCl3) δ: 167.1, 166.3, 142.3, 140.8, 130.8, 126.0, 120.5, 119.3, 60.9, 18.8, 14.4. ATR-IR (neat, $cm^{-1}$): v=3385 m (amide N—H), 2990 w (Ar—H), 1700 s (ester C=O), 1680 s (amide I), 1600 m (amide II), 1525 s (aromatic), 1285 s (ester C—O), 1252 s (ester C—O), 1170, 1120, 1104, 1023, 930, 854, 770. GC-MS (EI): m/z 69 (100%), 160 (47), 233 (M$^+$, 37), 188 (33), 119 (14).

Time-Lapse NMR.

An initial spectrum of IbuMA oligomer was recorded in $CDCl_3$ using a Bruker 500 MHz Spectrometer. One drop of deuterium oxide ($D_2O$, EMD Millipore) was then added and the sample inverted gently once to mix. Spectra were recorded immediately, then periodically for the next two hours.

Composition of TMA-BCA Adhesives.

A radical initiator-accelerator system used commonly in orthopedic medicine—BPO initiator with DMPT accelerator—was employed to allow free radical copolymerization of TMA and cyanoacrylate monomers to be initiated at 37° C. With the exception of skin adhesion experiments, substrates were pretreated with a 1% solution of HCl in ethanol to reduce the instance of anionic polymerization of BCA and mimic the acidic environment of skin and wounds. All TMA-BCA adhesives contained 10 wt % TMA, 5 wt % BPO initiator, and 0.1 wt % DMPT accelerator in Vetbond™, a BCA veterinary tissue adhesive produced by 3M. Vetbond™ is readily available, inexpensive, and chemically similar to the FDA-approved adhesives Indermil™, produced by Tyco Healthcare Group, LP, and Hystoacryl®, produced by TissueSeal. Thus, it serves as a useful model for clinical tissue adhesives.

Gel permeation chromatography (GPC) was performed on cured IbuMA-BCA adhesive using a Waters 2690 Separations Module equipped with three 5 μm Phenogel columns connected in series (guard, 105, 1000 and 100 Å) and a Waters 2487 dual A absorbance UV detector, calibrated against polystyrene standards, at 30° C. with chloroform as the eluent.

Covalent Controlled Release.

20 mL scintillation vials were pre-washed, then dried and pre-heated to 37° C. on a hot plate equipped with a thermocouple. 20 μL of an adhesive formulation was applied in the center bottom of each vial. Vials were capped and sealed; adhesives were cured for 24 h at 37° C. in a non-sterile incubator. At time t=0 h, 7 mL of either pH 4.9 sodium acetate buffer or pH 7 deionized water was added to each vial to submerge the adhesive. At each time point, 200 μL of the supernatant was removed from each vial and placed in a Greiner UV-clear 96 well plate for analysis using a Tecan Safire$^2$™ Plate Reader. Absorbance at 264 nm for IbuMA, 300 nm for AceMA and BenzMA was used to quantify the amount of drug released from each adhesive. In the case of IbuMA, since ibuprofen and BPO degradation products both absorb at 264 nm but ibuprofen does not absorb at 300 nm, absorbance from BPO degradation products was measured at 300 nm and used to correct the percent release of ibuprofen calculated for IbuMA. Each adhesive was tested in triplicate, i.e., three vials were prepared for each adhesive per pH condition. One measurement was taken from each vial for each time point. Vials were sealed thoroughly between measurements to prevent evaporation.

Quantification of Formaldehyde Release

Sample Preparation and Collection of Aliquots.

20 mL scintillation vials were pre-washed, then dried and pre-heated to 37° C. on a hot plate equipped with a thermocouple. 20 μL of an adhesive formulation was applied in the center bottom of each vial. Vials were capped and sealed; adhesives were cured for 24 h at 37° C. in a non-sterile incubator. One vial was prepared for each adhesive. At time t=0 h, 2 mL of deionized, degassed water was added to each vial to submerge the adhesive. At each time point, four 50 μL aliquots of the supernatant were removed from each vial and placed in a Greiner UV-clear 96 well plate for analysis.

Assay for the Quantification of Formaldehyde.

Solutions of formaldehyde in water (eight standards ranging in concentration from 0 to 300 μM), ammonium acetate in water (1 M), and acetoacetanilide in a 1:1 DMSO water mixture (0.6 mM) were prepared fresh on the day each time point was assayed. A Costar polystyrene 96-well plate was divided into three sections: "Standard" wells, "Sample" wells, and "Sample Background" wells. Standard wells were loaded with 40 μL ammonium acetate solution and 50 μL of a formaldehyde standard of known concentration. Standards were performed in duplicate. Sample wells were loaded with 40 μL ammonium acetate and 50 μL of sample supernatant. Sample Background wells were loaded with 40 μL ammonium acetate, 50 μL of sample supernatant, and 20 μL of deionized water. One well per sample was dedicated to sample background.

The reaction (which creates the fluorescent species) was then initiated by adding 20 μL of acetoacetanilide solution to every well except Sample Background wells. The well plate was then covered and placed in the dark to incubate at room temperature. After exactly 15 minutes from the addition of acetoacetanilide, the fluorescence intensity of each well was measured with a Tecan Safire$^2$™ plate reader by exciting samples at 370/20 nm and reading emission at 470/20 nm.

Bulk Mechanical Properties

Rheology.

Elastic moduli were determined using a TA Instruments Discovery HR-2 Rheometer, with a disposable plate geometry loaded with 8 mm aluminum plates outfitted with an environmental test chamber for temperature control. A total of three drops of adhesive were applied to the plates. Adhesives were spread thin to cover each plate so that mixing would be even, and the geometry was programmed to oscillate as the gap was set. Vetbond™-only controls were prepared by depositing Vetbond™ on the lower plate only. IbuMA-BCA adhesives were prepared by depositing an IbuMA-DMPT mixture on the upper plate and a Vetbond™-BPO mixture on the lower plate. AceMA-BCA and BenzMA-BCA adhesives were prepared by applying DMPT to the upper plate and a TMA-Vetbond™-BPO mixture to the lower plate. Data was recorded as soon as the gap was set and the sample quickly trimmed. Temperature was ramped from room temperature up to 37° C. Storage and loss moduli were monitored at 1 Hz and 1% strain until the storage modulus superseded the loss modulus and both moduli had stabilized, approximately 35 minutes. Elastic moduli were then determined through a frequency sweep experiment (0.1 Hz-100 Hz) performed at 37° C. The elastic modulus was taken as the average of the storage modulus at 1 Hz for at least three trials. In all cases the gap was set to approximately 500 μm, in order to consistently assess the curing behavior and mechanical properties of a thin layer of adhesive.

Lap Shear Mechanical Properties.

Lap shear strength of adhesives was assessed using an Instron Tensile Tester with a 50 kN load cell. Samples were prepared in accordance with ASTM D1002-10. Aluminum substrates 0.2 cm thick were trimmed to 2.5×10 cm strips, washed with isopropyl alcohol, and pre-treated. Substrates were then dried and pre-heated to 37° C. on a hot plate equipped with a thermocouple, and arranged with the upper and lower substrates apposed along the 2.5 cm side. For the IbuMA-BCA adhesive, a mixture of IbuMA and DMPT was applied to the 'upper' substrates, and a mixture of Vetbond™ (BCA) and BPO was applied to the 'lower' substrates. For AceMA- and BenzMA-BCA adhesives, DMPT was applied to 'upper' substrates, and a mixture of TMA, Vetbond™, and BPO was applied to 'lower' substrates. Each upper substrate was then immediately flipped and overlapped with a lower substrate by 2.5 cm. A weight was applied, and the substrates were allowed to cure overnight at 37° C.

Ex Vivo Wound Closure Ability.

Wound closure ability of TMA-BCA adhesives to adhere apposed sections of porcine cutaneous tissue under simulated biological conditions was tested according to ASTM F2458-05(2015), modeling wound closure. Freshly harvested porcine skin was washed with isopropyl alcohol and fresh phosphate buffered saline (PBS, #10010049, ThermoFisher Scientific), shaved, trimmed of subcutaneous fat and muscle, and cut into strips measuring 2.5 cm×10 cm×0.2 cm. At all times during preparation and experimentation, tissue was kept moist with PBS solution containing 5% v/v penicillin-streptomycin that had an initial concentration of 10,000 U/mL (#15140122, ThermoFisher Scientific).

Skin substrates (wrapped in PBS-soaked gauze and sealed in plastic bags) were primed by warming to 37° C. in a water bath for at least 15 minutes before use. To prepare one specimen, two strips of skin were removed from the water bath, blotted with sterile gauze, and placed on a hotplate equipped with a thermocouple set to 37° C. The two strips were apposed along one 2.5 cm side. Except in Vetbond™ (− BPO, DMPT) controls, the "wound area" around the apposed ends of the strips was blotted lightly with DMPT. Adhesive was then applied according to the Vetbond™ manufacturer's instructions, in a swirling motion across the wound area and in several layers. Samples were misted with PBS and allowed to cure for ten minutes on the warm hotplate surface before being braced, wrapped in gauze, and repackaged into sealed bags containing PBS. Specimens were placed back in the warm water bath to cure for another two hours prior to mechanical testing.

Five specimens were prepared for each adhesive. Precise length, width, and thickness of each specimen's adhesive area were measured with calipers and recorded prior to testing. Total specimen length between grips was measured after samples were loaded into the instrument. Mechanical properties of prepared specimens were assessed using an Instron Tensile Tester with a 50 kN load cell. The force was measured as the crosshead was raised at a rate of 30 mm/min until adhesive failure occurred.

Cytocompatibility

Cell Culture.

NIH-3T3 murine fibroblast cells were cultured in Dulbecco's Modified Eagle Medium with concentrations of 4,500 mg $L^{-1}$ for D-glucose, 584 mg $L^{-1}$ of L-glutamine, and 100 mg $L^{-1}$ sodium pyruvate that was supplemented with 10% v/v calf serum and 1% v/v penicillin-streptomycin that had an initial concentration of 10,000 U $mL^{-1}$. RAW 264.7 murine macrophages were cultured in similar media, except that the calf serum was replaced with fetal bovine serum. Both cell lines were maintained at 37° C. and a humidified atmosphere at 5% $CO_2$.

Scheme 1. Synthesis conditions for TMAs.

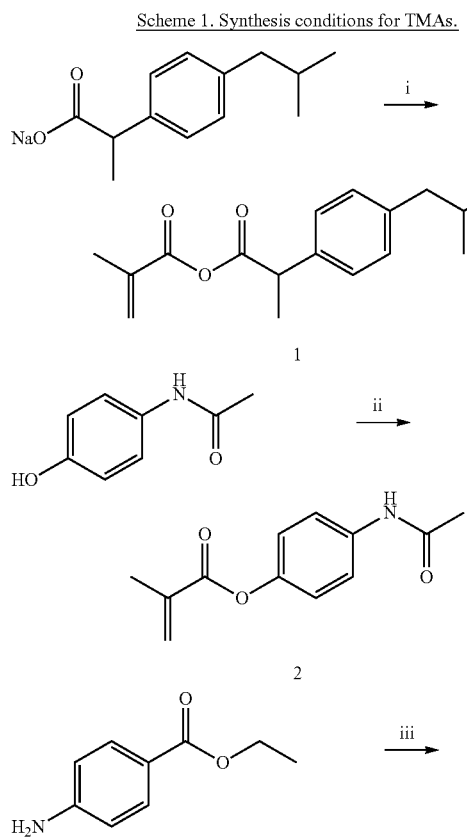

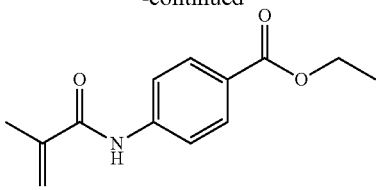

i) methacryloyl chloride, neat, 15° C. for 2 h, followed by excess ibuprofen sodium, hexanes, RT for 4 day, yielding IbuMA 1.
ii) methacrylic anhydride, TEA, DMAP, CHCl$_3$, 0° C. to RT over 12 h, yielding AceMA 2.
iii) methacryloyl chloride, K$_2$CO$_3$, CHCl$_3$, 0° C. to RT over 5 h, yielding BenzMA 3.

Cellular Vitality Analysis.

NIH-3T3 fibroblasts and RAW 264.7 macrophages were seeded at $3\times10^4$ and $2\times10^4$ cells $cm^{-2}$ in 96-well plates with 200 μL of media per well. After 24 h, the cells were exposed to adhesives in technical triplicates. For each well, 5 μL of adhesive monomer solution consisting of Vetbond™ with or without TMA monomers and BPO as indicated was rapidly mixed with 0.2 μL of DMPT accelerator (except for the Vetbond™ only control) and then immediately pipetted into the well, on top of the media. A solid visually formed on the order of seconds and typically remained at the air/liquid interface but was not large enough to prohibit gas transport. The cells were exposed to the adhesives for 24 h; then the cells were subjected to vitality analysis.

To assess cellular vitality, the cell culture media was carefully aspirated, and the cells were washed with phosphate buffered saline (PBS). Then, the cells were exposed to PBS containing 20 μM of Hoechst 33342 to label the DNA of all cell nuclei; 5 μM of Calcein AM to report cellular metabolism; and 2.5 μM of ethidium homodimer-1 to label the DNA of dead cells. After 10 min of incubation, the fluorescence intensity was determined by a fluorescence microplate reader (Tecan Safire²™) using excitations of 350/20 nm, 483/20 nm, and 525/20 nm and emissions of 461/20 nm, 525/20 nm, and 617/20 nm for Hoechst 33342, Calcein AM, and ethidium homodimer-1, respectively.

Fluorescence and phase-contrast imaging was performed on an EVOS® FL Auto Cell Imaging System with a 10×, 0.30 numerical aperture objective. Whole-well images were acquired using EVOS® FL Auto Cell Imaging Software. The adhesive materials resulted in a non-uniform level of background signal, making automatic image analysis challenging. Thus, proliferation was quantified by manually determining confluency from whole-well Hoechst 33342 fluorescence images.

Cytotoxicity.

NIH-3T3 fibroblasts and RAW 264.7 macrophages were seeded at $3\times10^4$ and $2\times10^4$ cells $cm^{-2}$ in 96-well plates with 200 μL media per well. After 6 h, 10 μL of 0.1% DMPT in complete cell culture media was added to each well for TMA-BCA adhesives and Vetbond™ (+) BPO, DMPT. Immediately, 20 μL of adhesive was added to the wells in quintuplet. The adhesives cured rapidly on contact with the media, forming a spherical mass in each well. In several wells, a small amount of adhesive then spread from the mass to cover the media surface in a thin film. To facilitate gas exchange at the media surface, a pipette tip was used to carefully push aside these very thin regions of adhesive, after allowing the adhesives to cure for 1 h. These regions were easily moved while the bulk of the adhesive was rigid and adhered in place. After 48 h in culture, cytotoxicity was specifically assessed using a lactate dehydrogenase (LDH) cytotoxicity kit according to manufacturer's recommendations and by fluorescently labeling detached cells in the media.

Lactate dehydrogenase (LDH) is a cytosolic enzyme that becomes released into the cellular media due to plasma membrane damage and is routinely used to determine cytotoxicity. LDH release was assessed using a commercially available assay kit (Pierce LDH Cytotoxicity Assay Kit, #88953, ThermoFisher Scientific). The LDH assay was run according to manufacturer's recommendations. Briefly, 50 µL of cell culture media was added to 50 µL of reaction mixture in a new 96-well plate and was allowed to incubate for 30 min at room temperature protected from light. Then, 50 µL of stop solution was added to each well, the plate was centrifuged at 1,000×g for 1 min to break up any bubbles, and then the absorbance was acquired from 300-800 nm with a 10 nm step size. The background absorbance at 680 nm was subtracted from the signal at 490 nm. Data is reported as %, as calculated by dividing the experimental well absorbance minus the spontaneous LDH release control (addition of deionized water) by the maximum LDH activity control (lysis of cells) minus the spontaneous LDH release control multiplied by 100%.

To further quantify cytotoxicity, from the same cell culture wells another 50 µL of cell culture media from each was aspirated and added in a new 96-well plate to 100 µL of staining solution containing 20 µM of Hoechst 33342 and 1.5 µM of propidium iodide. The samples incubated for 30 min; then, the fluorescence was assessed using a fluorescence microplate reader. Data is presented as feature scaled to the positive and negative controls for the LDH assay.

Statistical Analyses.

t-tests for unpaired samples with unequal variances and sample sizes were used to calculate p-values for differences compared to Vetbond™, or in the case of cellular vitality data, compared to Vetbond™ (+) BPO, DMPT. Differences were considered to be statistically significant when the p-value ≤ 0.05. Error bars displayed in the Figures in all cases represent the standard deviation of the value being measured.

Results and Discussion

Synthesis of TMAs and Formulation of TMA-BCA Adhesives.

Compared to industrial cyanoacrylate adhesives, medical cyanoacrylates contain longer, bulkier alkyl substituents that serve to moderate the rate of polymerization, reactivity of the monomers, and release of cytotoxic degradation products under aqueous conditions. TMAs have been designed so that a therapeutic and bioactive moiety, rather than a cytotoxic species, provides steric bulk to the monomers.

TMA monomers were synthesized through base-catalyzed coupling of therapeutic small molecules with nucleophilic carboxylate, hydroxyl, or primary amine functional groups to either methacryloyl chloride or methacrylic anhydride (Scheme 1). Monomers were characterized by $^1$H NMR (FIG. 9A) and $^{13}$C NMR, ATR FT-IR (FIG. 9B), GC-MS, and DSC.

Consistent with the trend in commercial medical adhesives of increasing cure time with increasing bulk of the monomer's substituents, cure time of TMA-BCA adhesives was found to follow the order IbuMA-BCA>AceMA-BCA>BenzMA-BCA>Vetbond™ (Table 1). IbuMA is the bulkiest TMA, and AceMA and BenzMA are roughly comparable to each other but bulkier than Vetbond™'s BCA monomer. IbuMA-BCA and AceMA-BCA have a statistically significant increase in average cure time compared to Vetbond™.

TABLE 1

Curing behavior of TMA-BCA adhesives compared to Vetbond ™.

| | Vetbond ™ (BCA) | IbuMA | AceMA | BenzMA |
|---|---|---|---|---|
| Gel time (s) | 40 ± 10 | 300 ± 100 | 12 ± 6 | 10 ± 4 |
| Cure time (s) | 400 ± 100 | 1700 ± 100 | 800 ± 200 | 700 ± 200 |

Gel time was not found to follow the same trend with monomer bulkiness, but was instead strongly influenced by the method used to apply adhesives to the parallel plate substrates. To cure AceMA-BCA and BenzMA-BCA adhesives onto the parallel plate geometry, AceMA and BenzMA monomers, solid at room temperature, were dissolved in Vetbond™ along with initiator BPO and only brought into contact with the accelerator DMPT when cure was to be initiated. The resulting AceMA-BCA and BenzMA-BCA adhesives show a shorter gel time compared to Vetbond™, which may be due to rapid nucleophilic initiation of a small portion of Vetbond™ upon contact with DMPT. However, this rapid gelation is followed by a steadier, slower increase in the shear storage modulus not seen in the cure of the Vetbond™ control. The slower, secondary cure of AceMA-BCA and BenzMA-BCA adhesives is attributed to slower radical initiation of polymers containing BCA and TMAs.

Unlike AceMA and BenzMA monomers, IbuMA is a viscous liquid at room temperature. However, the mixture containing IbuMA, Vetbond™, and BPO was found to be insufficiently stable to allow the IbuMA-BCA adhesive to be delivered in the same way as AceMA-BCA and BenzMA-BCA adhesives. Thus, for IbuMA-BCA, BPO was dissolved in Vetbond™, and DMPT was dissolved in IbuMA monomer. These two mixtures were brought together when cure was to be initiated. Compared to both the Vetbond™ control and AceMA-BCA and BenzMA-BCA adhesives, IbuMA-BCA shows an increased gel time. The viscosity of the IbuMA monomer is suspected to contribute to the longer gel time of the IbuMA-BCA adhesive. Sample preparation and adhesive application to substrates can be optimized to control the gel time in future applications.

Covalent Controlled Release.

To determine the rates of release of the small therapeutic molecules of ibuprofen, acetaminophen, or benzocaine from the TMA-BCA adhesives, cured adhesives were submerged in either neutral water or pH 5 buffer that mimicked the acidity of skin. Covalent controlled release of therapeutics from model TMA-BCA adhesives was shown to follow the order anhydride (IbuMA-BCA)>ester (AceMA-BCA)>amide (BenzMA-BCA), as predicted by the susceptibility of these bond types to hydrolysis (FIG. 2). Correspondingly, the initial rate constant of therapeutic release was calculated for the buffered acidic conditions and varies dramatically according to tether bond type. Assuming pseudo-first order kinetics in the first few hours after being submerged in acidic buffer, the rate constants of release from IbuMA-BCA, AceMA-BCA, and BenzMA-BCA adhesives were found to be significantly different: 1300±700, 110±30, and 40±10 $M^{-1} h^{-1}$, respectively (FIG. 10). The range of release rate constants achieved here highlights the promise of covalent controlled release as a platform technology for dynamic drug delivery from tissue adhesives.

Covalent controlled release was observed in both acidic and neutral/unbuffered conditions. Greater therapeutic release was observed at pH 4.9, which is approximately the pH of skin and most healing wounds, for the ester- and amide-containing adhesives AceMA-BCA and BenzMA-BCA than in neutral conditions. Enhanced hydrolysis of esters and amides in acidic conditions is consistent with the classic arrow-pushing mechanisms of carbonyl hydrolysis: in the absence of catalytic acid, the leaving groups of esters and amides are strongly basic anions (alkoxy and amine species) and so their formation is unfavorable. Under acidic conditions, however, protonation of the oxygen of the carbonyl and of the heteroatom of the leaving group can facilitate hydrolysis by activating the carbonyl to nucleophilic attack and by making the leaving group a neutral, rather than anionic, species. Unlike the ester- and amide-containing TMA-BCAs, the anhydride-containing IbuMA-BCA adhesive showed slightly greater release under neutral, unbuffered conditions compared to buffered acidic conditions. This is consistent with the autocatalytic mechanism of anhydride hydrolysis that does not require the addition of protons to proceed favorably.

In the case of AceMA-BCA and BenzMA-BCA, the ester and amide tethers show more similar release profiles than might be expected for simple esters versus amides due to electronic contributions from other substituents on these TMAs. Particularly, BenzMA-BCA demonstrates greater hydrolytic release of benzocaine than might be expected for an amide tether because 1) benzocaine is an aromatic amine, which improves its leaving group ability compared to an alkyl amine, and 2) benzocaine contains an electron-withdrawing ester group para to the amine which further improves benzocaine's leaving group ability.

Per one gram of 10% TMA-BCA adhesive, enough to cover the surface of a small laceration, IbuMA-BCA was calculated to release 12±6 mg ibuprofen in the first 3.4 hours after application under acidic conditions; AceMA-BCA released 1.5±0.9 mg acetaminophen and BenzMA-BCA released 0.4±0.1 mg benzocaine. Release of ibuprofen from IbuMA-BCA adhesives is on the same magnitude and time scale as release of ibuprofen from commercially available topical medications. Release from AceMA-BCA and BenzMA-BCA adhesives as formulated here is somewhat lower and may not be as effective as the IbuMA-BCA adhesive at providing pain relief, particularly considering topical adhesives may not be continuously hydrated when used clinically as they were in this experiment. However, application of the TMA-BCA adhesives directly to healing wounds is expected to facilitate diffusion of the therapeutics past the stratum corneum, the main barrier of the skin, improving their ability to provide pain relief in a clinical setting. Further, the amount of therapeutic released can potentially be controlled by adjusting the TMA loading of the adhesive. This is especially true in the case of the BenzMA monomer, which was observed during preliminary formulation tests to have excellent solubility in BCA monomer even at 25% TMA by weight in the adhesive.

Covalent controlled release of therapeutics from TMA-BCA adhesives was only observed when TMA monomers underwent polymerization (FIG. 11). When TMAs are mixed into Vetbond™ but the radical initiator-accelerator (BPO-DMPT) system is omitted, so that Vetbond™ will polymerize through its anionic mechanism but TMA monomers will not polymerize, dramatically less of the therapeutics is detected in the supernatant above submerged adhesives (FIG. 11C,D). However, covalent controlled release has been observed for free TMA monomers in solution: the hydrolysis of ibuprofen from IbuMA dissolved in CDCl$_3$ has been observed with $^1$H NMR. Spectra acquired over time show a change in the pattern of both vinylic and aromatic protons that reflect anhydride bond hydrolysis from IbuMA monomers over the course of 90 min after exposure to D$_2$O (FIG. 12). Hydrolysis of AceMA and BenzMA monomers has not been characterized by NMR due to their significantly slower hydrolysis versus IbuMA, though these TMAs are also expected to freely undergo hydrolysis when in solution.

The implications of this are twofold. First, uncured TMA monomer is not observed to leach out of the cured adhesive matrix in appreciable amounts. Increased steric bulk has previously been reported in the literature to decrease leaching of uncured methacrylate monomers from a partially cured methacrylate resin; it would be reasonable for uncured TMA monomers within a cured cyanoacrylate matrix to be similarly trapped, as long as the cyanoacrylate matrix remains intact. (Internally in vivo, it can take over a year for a mass of BCA adhesive to degrade.) Second, simultaneous radical polymerization of TMA and BCA monomers, rather than simple mixing of TMAs into a BCA adhesive, appears to be necessary for covalent controlled release of therapeutics from TMAs. TMA monomers that undergo simultaneous polymerization alongside BCA are hypothesized, without intent to be bound by this, to be more available to the aqueous environment compared to TMA monomers trapped within a hydrophobic BCA homopolymer matrix. Interestingly, release of ibuprofen from the IbuMA-BCA adhesive was also found to be greater and more sustained than the elution of ibuprofen noncovalently loaded into a cyanoacrylate adhesive (FIG. 11B), further suggesting the potential benefits of TMA adhesives as vehicles for the controlled delivery of therapeutics.

The cured IbuMA-BCA adhesive, which is somewhat more soluble in organic solvents than other TMA-BCA adhesives, has been characterized by GPC and $^1$H NMR. By chloroform GPC, the soluble fraction of IbuMA-BCA was found to be multimodal, with the highest detectable molecular weight distribution having $M_n$=4.83×10$^5$ Da and Đ=2.44. The $^1$H NMR spectrum of cured IbuMA-BCA adhesive (FIG. 13) shows complete disappearance of the vinylic protons that are present only in the monomers, suggesting polymerization continued to completion for both IbuMA and BCA. The corresponding characterization of AceMA-BCA and BenzMA-BCA adhesives is ongoing.

Reduced Formaldehyde Generation.

Free radical copolymerization of cyanoacrylate and methacrylate monomers has been shown in the literature to increase the stability of the resulting copolymer to aqueous and thermal degradation compared to anionically-initiated cyanoacrylate homopolymers. Additionally, radical polymerization of cyanoacrylates can decrease the presence of acidic end groups (which are vulnerable points to aqueous degradation) and influence the polymer molecular weight compared to anionic polymerization, by virtue of the distinct termination pathways that occur in radical versus anionic polymerization. Thus, the radical polymerization of BCA and TMAs that occurs in the curing of TMA-BCA adhesives is expected to influence the aqueous degradation of these materials compared to typical cyanoacrylate adhesives.

To characterize the aqueous degradation of TMA-BCA adhesives, we measured the amount of formaldehyde, a common product of BCA degradation, present in the supernatant above TMA-BCA adhesives submerged in water. All TMA-BCA adhesives showed a decrease in formaldehyde release compared to Vetbond™ (FIG. 3). TMA-BCA adhesives showed between 25 and 50% reduction in formaldehyde present at 79 h after submersion in water and between 66 and 77% reduction at 220 h compared to Vetbond™.

Notably, radical polymerization of Vetbond™ by BPO-DMPT was also observed to reduce the release of formaldehyde (not shown). Characterization of the mechanisms by which TMA-BCA adhesives may suppress formaldehyde release is ongoing, but is believed to be related to the stability of polymer end groups and the molecular weight distribution compared to anionically-polymerized Vetbond™.

The decline in formaldehyde concentration seen after 79 h for all adhesives is attributed to the lability of formaldehyde, which may become unavailable to detection by the selected assay by either evaporation, or reaction with components of the adhesives or supernatant. The decline in formaldehyde concentration is noticeably greater for TMA-BCA adhesives compared to Vetbond™.

Though anionic polymerization can be suppressed, complete elimination of anionic polymerization of BCA is challenging, especially under ambient and biological conditions. Anionic initiation of BCA by trace nucleophiles can result in BCA oligomers that are especially susceptible to aqueous degradation. For all adhesives, a rapid release of formaldehyde was observed up to 79 h; however, the release of formaldehyde from TMA-BCA adhesives was observed to be lower than that from Vetbond™, suggesting that less of the adhesive sample was susceptible to this rapid degradation. Continued optimization of the curing system for TMA-BCA adhesives to further suppress anionic polymerization is anticipated to further reduce the formaldehyde generated by these adhesives.

Cytocompatibility.

Cytocompatibility of TMA-BCA adhesives was tested by curing 20 μL of each adhesive formulation in situ in the cell culture media above murine NIH-3T3 fibroblasts or RAW 264.7 macrophages. The selected cell types are present in healing cutaneous tissue and should therefore give a preliminary indication of cytocompatibility. These cell lines have a doubling time on the order of one day, so to maximize the sensitivities of the assays, the experiments were designed such that cells were approaching confluency at the experiments' conclusions. Adhesives were introduced to and cured within the media in contact with cells, and cells were incubated in the presence of these adhesives. This exposure method was chosen to capture the major sources of acrylate cytotoxicity, including oxidative stress and exothermicity during curing, and release of formaldehyde shortly after curing.

Though the radical initiator-accelerator system BPO-DMPT is widely used in orthopedic cements, it is not typically present in cyanoacrylate-based soft tissue adhesives. Cyanoacrylate monomers can undergo radical polymerization if the appropriate radical initiator is present, but do not require an added initiator to undergo their more characteristic anionic polymerization under ambient conditions. Methacrylic monomers, however, cannot undergo anionic polymerization under ambient conditions, but can easily undergo radical polymerization with the appropriate initiator present; hence, the BPO-DMPT system was used to initiate a relatively mild polymerization of both TMA and BCA monomers in our adhesives. The BPO-DMPT system's influence on the cytocompatibility of the adhesives was therefore characterized separately from the therapeutic TMA component. Thus, we included both Vetbond™ (−) and Vetbond™ (+) BPO, DMPT controls in the assessment of cytocompatibility.

Typically, cytocompatibility is assessed using a combination of fluorescent reporters. However, Vetbond™ and the TMA-BCA adhesives substantially interfered with our fluorescence assays, as shown in fluorescence images that contain considerable signal from the adhesives (not shown). This background signal is attributed primarily to light scattering by the bulk adhesive material rather than autofluorescence of the polymers, as the adhesives were observed to be turbid with uneven surfaces, and background signal during imaging was found to be highly dependent on the angle of the contours of bulk adhesive in any sample. Though cyanoacrylate polymers are not intrinsically fluorescent (although most cyanoacrylate tissue adhesives do contain a small amount of dye to help surgeons visualize placement of the adhesive), Vetbond™ has been previously reported to interfere with imaging. Ultimately, the high background signal caused by the adhesives prohibited the determination of cytotoxicity using the Calcein AM assay for cellular metabolism and the ethidium homodimer-1 assay for dead cells, which rely on accurate fluorescence intensity. Thus, cellular proliferation was focused upon, because cellular nuclei could be quantified independently of fluorescence intensity, and LDH release, because aliquots of media would be assessed in fresh wells away from adhesives.

To overcome the highly non-uniform background signal while assessing cellular proliferation, fluorescent images of cell nuclei labeled with Hoechst 33342 were acquired (FIG. 5A) and concatenated them into a large image of the entire well using our microscope's automation (not shown). From these whole-well images, cellular confluency was quantified (FIG. 5B) using a grading scale similar to that used to assess histological samples. To assess cytotoxicity, aliquots of the cell media were aspirated and quantified the detached cells (FIG. 5C) and LDH release (FIG. 5D).

Generally, cells exposed to any adhesive material showed reduced confluency and an increase in the number of detached cells compared to no treatment controls, indicating that both Vetbond™ and TMA-BCA adhesives reduce cellular proliferation and possess moderate cytotoxicity. However, there was no reduction in cellular vitality between Vetbond™ (+) BPO, DMPT and Vetbond™ (−) BPO, DMPT, suggesting the BPO-DMPT system had minimal impact on the cytocompatibility of the TMA-BCA adhesives. Further, cells exposed to the TMA-BCA adhesives showed similar if not significantly higher confluency compared to those exposed to Vetbond™ (+) BPO, DMPT.

Specifically, NIH-3T3 fibroblasts exposed to the TMA-BCA adhesives showed comparable proliferation to that of cells exposed to Vetbond™ (+) BPO, DMPT and, for BenzMA-BCA, had a significant reduction in the number of detached cells. Additionally, RAW 264.7 macrophages exposed to the AceMA-BCA and BenzMA-BCA adhesives showed a significantly smaller reduction in proliferation than cells exposed to Vetbond™ (+) BPO, DMPT. We note that there were increases in detached cells for both NIH-3T3 fibroblasts and RAW 264.7 macrophages exposed to IbuMA-BCA, but there was a corresponding decrease in LDH release making the overall effect on cytotoxicity similar to Vetbond™ (+) BPO, DMPT.

Overall, the recovery in cellular confluency for TMA-BCA adhesives compared to the Vetbond™ controls may be due to the reduction in formaldehyde release by the TMA-BCA adhesives compared to Vetbond™ (−) BPO, DMPT. Additionally, the covalent controlled release of anti-inflammatory therapeutics may prevent the activation of macrophages that results in reduced proliferation.

Mechanical Properties of TMA-BCA Adhesives

Shear Moduli.

The stiffness of an adhesive has been shown in the literature to dramatically affect its adhesive ability, with adhesives often performing best when matched with substrates of a similar stiffness. This effect has been found to be most pronounced for low moduli substrates, like skin and other soft tissues, where modulus match between adhesive and substrate can prevent stress from concentrating at the adhesive-substrate interface. Exact modulus match becomes less vital for effective adhesion to very stiff substrates like aluminum, where instead, the toughness of the adhesive and its ability to deform plastically without failing dominate. Thus, the effects of TMA monomers on the stiffness of TMA-BCA adhesives were determined by rheometry.

TMA-BCA adhesives were found to cover a broad range of moduli (FIG. 7). At 0.6±0.4 MPa, the shear storage modulus of IbuMA-BCA is the lowest and the closest of all adhesives to that of porcine skin, measured by Fleck et al. to be 1.5 MPa under similar conditions (O. A. Shergold, et al., *Int. J. Impact Eng.*, 2006, 32, 1384-140). By contrast, the shear storage moduli of AceMA-BCA and BenzMA-BCA, which contain rigid aromatic amide groups, are higher. The shear storage modulus measured for AceMA-BCA is surprisingly high, being an order of magnitude greater than both Vetbond™ and BenzMA-BCA, but is well within the range of hard tissues such as bone (289±183 MPa), suggesting AceMA-BCA may be a useful hard-tissue adhesive. Interestingly, IbuMA could potentially be used as a "neat" adhesive because its monomer is a liquid at room temperature and thus does not need to be dissolved in another comonomer to act as an adhesive. Neat IbuMA adhesive has a shear storage modulus of 0.26±0.05 MPa, roughly half that of the IbuMA-BCA adhesive (not shown).

Lap Shear Adhesion.

Lap shear is one of the most common methods to characterize bulk adhesion of adhesive materials, and aluminum substrates are frequently used when evaluating adhesives as aluminum is considerably stiffer and has a higher tensile strength than adhesives, enabling characterization of the adhesive without contribution from deformations in the substrate. In this case, the use of aluminum substrates also enabled the evaluation of TMA-BCA adhesive properties without the influence of water or nucleophiles associated with cutaneous tissue on curing. BenzMA-BCA shows a considerable increase in both lap shear strength (FIG. 8A) and ductility (FIG. 8B) compared to the Vetbond™ control, even at only 10% TMA loading. The gains in both strength and ductility translate into a 219% increase in toughness of BenzMA-BCA over Vetbond™ (FIG. 8C) and ductility (FIG. 8B). In a clinical setting, the increase in toughness observed for BenzMA-BCA adhesives over Vetbond™ would reduce the instance of wound dehiscence due to adhesive cracking, because of the TMA-BCA adhesive's ability to withstand greater loads and deform plastically without failing (FIG. 8D).

AceMA-BCA has comparable lap shear strength to Vetbond™, but is on average not as ductile, leading to a statistically insignificant decrease in toughness. IbuMA-BCA shows a decrease in lap shear strength and ductility compared to Vebond™, which may be a result of its sensitivity to moisture. Optimizing the formulation of IbuMA-BCA and AceMA-BCA adhesives may improve their performance. In both cases, IbuMA-BCA and AceMA-BCA adhesives may prove to be more effective at lower TMA loadings; characterization of different TMA-BCA formulations is ongoing.

Adhesion to Porcine Skin.

Adhesion to two apposed sections of porcine skin was used as to model wound closure ability and wound burst strength for TMA-BCA adhesives ex vivo. All TMA-BCA adhesives demonstrated similar adhesion to skin compared to Vetbond™ (FIG. 6). Interestingly, in skin adhesion tests, the IbuMA-BCA adhesive performed comparably to Vetbond™ even though it did not perform as well in lap shear experiments.

Extensive literature describes the benefit of mechanical match between substrate and adhesive when adhering two surfaces, particularly for soft substrates. n-butyl cyanoacrylate tissue adhesives like Vetbond™ tend to be both stiffer and more brittle than the soft cutaneous tissue they are used to repair. The difference in mechanical properties between skin and brittle adhesives can concentrate stresses at the adhesive-tissue interface, leading to adhesive failure. The similarity between the shear moduli of IbuMA-BCA adhesive (0.6±0.4 MPa) and porcine skin (1.5 MPa) may contribute to the enhanced adhesion of the IbuMA-BCA adhesive to skin compared to aluminum (26 GPa) by more evenly distributing the stresses experienced by the skin without creating focal points at the adhesive-tissue interface. Likewise, the exceptionally stiff AceMA adhesives (60±20 MPa) displayed the weakest adhesion to skin, despite showing strong adhesion, comparable to Vetbond™, to aluminum.

Optimizing the formulation of TMA-BCA adhesives is expected to further improve their performance in future ex vivo and in vivo settings and will be vital moving forward. Further, the presence of moisture in ex vivo, in vivo, and clinical settings may affect not just the curing of TMA-BCA adhesives but also their mechanical robustness over time. The cotton fabric peel test, in which PBS-soaked cotton strips form the substrates for an adhesive peel test, may be useful for characterizing the specific effects of moisture on TMA-BCA adhesives over time and for optimizing these adhesives before moving to in vivo experiments.

Example 6—Controlled Release of Therapeutics from TMA-MMA Adhesives

TMA-MMA adhesives are two-component adhesives. Component A contains TMA monomer, methyl methacrylate (MMA), and benzoyl peroxide (BPO). Component B contains MMA and dimethyl-p-toluidene (DMPT). When components A and B are combined, the adhesive cures. Cure is very slow at room temperature and more rapid at 37° C. Equal parts of component A and component B are applied to the substrate to create the complete adhesive. In this experiment, the complete adhesive (A+B) contains 10% by mass TMA, 5% by mass BPO, 0.1% by mass DMPT, and 84.9% MMA.

20 mL scintillation vials were washed with methanol, dried, and pre-heated to 37° C. on a hot plate equipped with a thermocouple. Adhesive formulations were applied in the center bottom of each vial dropwise. Vials were capped and sealed; adhesives were then cured for 24 h at 37° C. in a non-sterile incubator. At time t=0 h, 7 mL of pH 7 deionized water was added to each vial to submerge the adhesive. At each time point, 200 µL of the supernatant was removed from each vial and placed in a Greiner UV-clear 96 well plate for analysis. Absorbance at 302 nm for SalMA, AceMA, and BenzMA was used to quantify the amount of drug released from each adhesive. Each adhesive was tested in quintuplicate, i.e., five vials were prepared for each adhesive. One measurement was taken from each vial for each time point. Vials were sealed thoroughly between measurements to prevent evaporation.

Covalent controlled release of salicylic acid (from SalMA-MMA, an electron-poor ester), acetaminophen (from AceMA-MMA, an electron-rich ester), or benzocaine (from BenzMA-MMA, an electron-poor amide) in neutral (pH 7 deionized water) conditions. Percent release represents the amount of therapeutic detected in the supernatant above submerged adhesives divided by equivalents of therapeutic carried in the TMA-MMA adhesive.

FIG. 14 contains data analogous to FIG. 2B. This figure shows that the covalently-controlled release of therapeutics from the TMAs is possible from an adhesive with a methyl methacrylate base in addition to the butyl cyanoacrylate base of TMA-BCA adhesives shown in FIG. 2B. The rate of release of the therapeutic from the TMA-MMA adhesive is directly related to the susceptibility of the TMA's tether bond to hydrolysis, i.e., the ester tethers are released more quickly than the amide tether.

This also demonstrates that the electronic properties of the therapeutic (whether the tether bond is electron-rich or electron-poor) can be used to influence the rate of release of the therapeutic from a TMA adhesive. i.e., the electron-poor ester of the SalMA is more susceptible to hydrolysis than the electron-rich ester of the AceMA, and correspondingly, the salicylic acid is released from the SalMA-MMA adhesive more quickly than the acetaminophen is released from the AceMA-MMA adhesive.

Mechanical Properties of TMA-MMA Adhesives—Shear Storage Moduli.

As in the controlled release experiment, adhesives were formulated to act as two-component adhesives. In this experiment, the complete adhesive (component A+component B) contains 10% by mass TMA, 5% by mass BPO, 0.1% by mass DMPT, and 84.9% MMA. Component A contained TMA, BPO, and MMA; component B contained DMPT and MMA. Equal parts of components A and B were combined to create the complete adhesive. Control samples BCA (Vetbond™, used as intended by manufacturers, with no additional initiator added) and MMA (a two-component adhesive formulated to be identical to the TMA-MMA adhesives but in which the 10% by mass of TMA was replaced with additional MMA) were also tested for comparison.

Storage moduli, which provide an indication of the elastic moduli, were determined using a TA Instruments Discovery HR-2 Rheometer, with a disposable plate geometry loaded with 25 mm aluminum plates outfitted with an environmental test chamber for temperature control. Six drops of adhesive were applied to the plates in total, three drops of each component. For TMA-MMA adhesives, component A, containing TMA, BPO, and MMA, was applied to the lower plate, and component B, containing DMPT and MMA, was applied to the upper plate. For the BCA control adhesive, Vetbond™ was applied to the lower plate only. For the MMA control adhesive, component A, containing BPO and MMA, was applied to the lower plate, and component B, containing DMPT and MMA, was applied to the upper plate. For all samples, adhesives were spread thin to cover the plate, and the geometry was programmed to oscillate as the gap was set to facilitate mixing.

Data was recorded as soon as the gap was set and the sample quickly trimmed. Temperature was ramped from room temperature up to 37° C. Storage and loss moduli were monitored at 1 Hz and 1% strain until the storage modulus superseded the loss modulus and both moduli had stabilized, approximately 45 minutes. Elastic moduli were then determined through a frequency sweep experiment (0.1 Hz-100 Hz) performed at 37° C. The elastic modulus was taken as the average of the storage modulus at 1 Hz for at least three trials. In all cases the gap was set to approximately 50 μm, in order to consistently assess the curing behavior and mechanical properties of a thin layer of adhesive.

FIG. 15 indicates that the stiffness of TMA-MMA adhesives is tunable according to the type of therapeutic present in the TMA, but also that TMA-MMA adhesives have stiffnesses well within an acceptable range for tissue adhesives, as TMA-MMA adhesives show comparable moduli to common adhesive materials BCA and MMA.

Example 7—Mesalazine MA

Amide-tethered mesalazine MA (amide-MES-MA) is created by nucleophilic carbonyl substitution under basic conditions. Mesalazine and an activated methacrylate such as methacryloyl chloride is combined in solution, then a base, such as triethylamine, is added. Here, there is the possibility that the hydroxyl and carboxylic acid groups could also act as nucleophiles, but the amine group is expected to outcompete these other groups as the strongest nucleophile. Column chromatography is used to isolate the desired amide-tethered mesalazine MA from any ester-tethered MA that is produced.

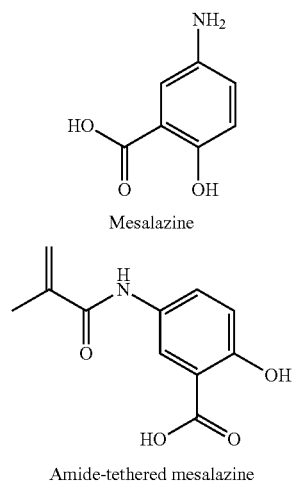

Mesalazine

Amide-tethered mesalazine

For ester-tethered MES-MA, the amine of mesalazine is first protected with an FMOC group. Then the nucleophilic carbonyl substitution is conducted using a base such as potassium carbonate and an activated methacrylate such as methacryloyl chloride. The procedure reported above for the synthesis of ACE-MA, involving the use of methacryloyl anhydride, triethylamine, and catalytic dimethylaminopyridine, is also expected to be successful. In either case, the ester-tethered product is isolated by column chromatography, then the FMOC protecting group is removed to reveal the free amine in ester-MES-MA.

For anhydride-tethered MES-MA, a weak base such as dilute sodium bicarbonate is used to ensure that the carboxylic acid group is the only group that is deprotonated. A short reaction time at low temperature, and a strongly activated methacrylate such as methacryloyl chloride is used for the nucleophilic carbonyl substitution (the methacryloyl anhydride would not be effective here). The product is washed rapidly with dilute aqueous base to remove unreacted mesalazine with free carboxylic acid groups, then column chromatography is performed under dry conditions (such as in a glove box) in order to isolate the anhydride-MES-MA.

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

What is claimed is:

1. A compound having the following structure:

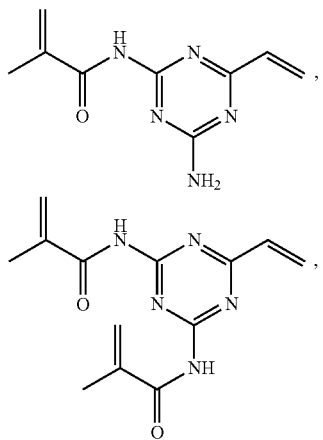

or a pharmaceutically-acceptable salt thereof.

2. The compound of claim 1, having the structure:

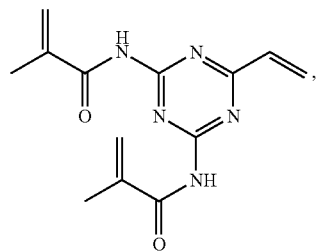 [SMILES: C=Cc1nc(NC(=O)C(=C)C)nc(NC(=O)C(=C)C)n1]

or a pharmaceutically-acceptable salt thereof.

3. The compound of claim 1, having the structure:

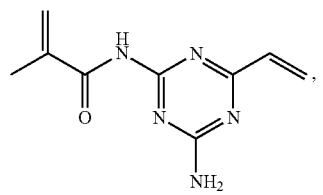

or a pharmaceutically acceptable salt thereof.

4. A composition, comprising the compound of claim 1, and an adhesive.

5. The composition of claim 4, further comprising an acrylate adhesive.

6. The composition of claim 5, wherein the acrylate adhesive is one or more of a methacrylate adhesive and a cyanoacrylate adhesive.

7. The composition of claim 5, wherein the acrylate adhesive is a 2-cyanoacrylate adhesive.

8. The composition of claim 5, wherein the acrylate adhesive has the structure:

where $R_3$ is a $C_1$-$C_{12}$ saturated hydrocarbon, and includes branched, unbranched and cyclic structures, or combinations thereof.

9. The composition of claim 8, wherein the acrylate adhesive is methyl-2-cyanoacrylate, ethyl-2-cyanoacrylate, n-butyl cyanoacrylate, or 2-octyl cyanoacrylate.

10. A method of treating a patient, comprising joining bone tissue or joining bone tissue with a prosthetic in the patient with an acrylic adhesive comprising a composition as claimed in claim 4.

11. The method of claim 10, wherein the adhesive is used in a bone cement that is applied to bone and/or a prosthetic implanted in the patient.

12. The composition of claim 4, wherein the compound has the structure:

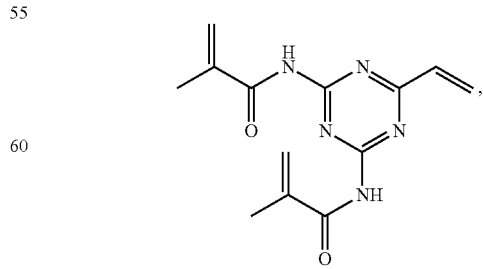

or a pharmaceutically-acceptable salt thereof.

13. The composition of claim 4, wherein the compound has the structure:
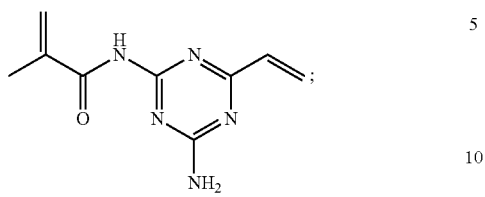
or a pharmaceutically acceptable salt thereof.
* * * * *

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: cell adhesion peptide

<400> SEQUENCE: 1

Ile Lys Val Ala Val
1               5

<210> SEQ ID NO 2
<211> LENGTH: 4
<212> TYPE: PRT
<213> ORGANISM: Artificial Sequence
<220> FEATURE:
<223> OTHER INFORMATION: cell adhesion peptide

<400> SEQUENCE: 2

Arg Gly Asp Ser
1

<210> SEQ ID NO 3
<211> LENGTH: 6
<212> TYPE: PRT
<213> ORGANISM: Artificial Sequence
<220> FEATURE:
<223> OTHER INFORMATION: cell adhesion peptide

<400> SEQUENCE: 3

Lys Gln Ala Gly Asp Val
1               5

<210> SEQ ID NO 4
<211> LENGTH: 6
<212> TYPE: PRT
<213> ORGANISM: Artificial Sequence
<220> FEATURE:
<223> OTHER INFORMATION: cell adhesion peptide

<400> SEQUENCE: 4

Val Ala Pro Gly Val Gly
1               5

<210> SEQ ID NO 5
<211> LENGTH: 6
<212> TYPE: PRT
<213> ORGANISM: Artificial Sequence
<220> FEATURE:
<223> OTHER INFORMATION: cell adhesion peptide

<400> SEQUENCE: 5

Ala Pro Gly Val Gly Val
1               5

<210> SEQ ID NO 6
<211> LENGTH: 6
<212> TYPE: PRT
<213> ORGANISM: Artificial Sequence
<220> FEATURE:
<223> OTHER INFORMATION: cell adhesion peptide

<400> SEQUENCE: 6

Pro Gly Val Gly Val Ala
1               5
```

```
<210> SEQ ID NO 7
<211> LENGTH: 5
<212> TYPE: PRT
<213> ORGANISM: Artificial Sequence
<220> FEATURE:
<223> OTHER INFORMATION: cell adhesion peptide

<400> SEQUENCE: 7

Gly Val Gly Val Ala
1               5

<210> SEQ ID NO 8
<211> LENGTH: 4
<212> TYPE: PRT
<213> ORGANISM: Artificial Sequence
<220> FEATURE:
<223> OTHER INFORMATION: cell adhesion peptide

<400> SEQUENCE: 8

Val Ala Pro Gly
1

<210> SEQ ID NO 9
<211> LENGTH: 6
<212> TYPE: PRT
<213> ORGANISM: Artificial Sequence
<220> FEATURE:
<223> OTHER INFORMATION: cell adhesion peptide

<400> SEQUENCE: 9

Val Gly Val Ala Pro Gly
1               5

<210> SEQ ID NO 10
<211> LENGTH: 4
<212> TYPE: PRT
<213> ORGANISM: Artificial Sequence
<220> FEATURE:
<223> OTHER INFORMATION: cell adhesion peptide

<400> SEQUENCE: 10

Val Gly Val Ala
1

<210> SEQ ID NO 11
<211> LENGTH: 5
<212> TYPE: PRT
<213> ORGANISM: Artificial Sequence
<220> FEATURE:
<223> OTHER INFORMATION: cell adhesion peptide

<400> SEQUENCE: 11

Val Ala Pro Gly Val
1               5

<210> SEQ ID NO 12
<211> LENGTH: 6
<212> TYPE: PRT
<213> ORGANISM: Artificial Sequence
<220> FEATURE:
<223> OTHER INFORMATION: cell adhesion peptide

<400> SEQUENCE: 12

Gly Val Ala Pro Gly Val
1               5
```

```
<210> SEQ ID NO 13
<211> LENGTH: 4
<212> TYPE: PRT
<213> ORGANISM: Artificial Sequence
<220> FEATURE:
<223> OTHER INFORMATION: cell adhesion peptide

<400> SEQUENCE: 13

Asp Gly Glu Ala
1
```